US012708762B2

(12) United States Patent
Scott-Young et al.

(10) Patent No.: US 12,708,762 B2
(45) Date of Patent: Aug. 18, 2026

(54) COMBINED LIGHT AND ELECTRICAL STIMULATION OF LIGHT-SENSITIVE NEURAL TISSUE

(71) Applicant: THE BIONICS INSTITUTE OF AUSTRALIA, East Melbourne (AU)

(72) Inventors: Rachael Scott-Young, East Melbourne (AU); James Fallon, East Melbourne (AU); Andrew Wise, East Melbourne (AU); Alexander Thompson, East Melbourne (AU); Paul Randall Stoddart, Hawthorn (AU); William Lloyd Hart, Hawthorn (AU); Karina Brady, Melbourne (AU)

(73) Assignee: THE BIONICS INSTITUTE OF AUSTRALIA, East Melbourne (AU)

( * ) Notice: Subject to any disclaimer, the term of this patent is extended or adjusted under 35 U.S.C. 154(b) by 581 days.

(21) Appl. No.: 17/622,511

(22) PCT Filed: Jun. 26, 2020

(86) PCT No.: PCT/AU2020/050653

§ 371 (c)(1),
(2) Date: Dec. 23, 2021

(87) PCT Pub. No.: WO2020/257864

PCT Pub. Date: Dec. 30, 2020

(65) Prior Publication Data

US 2022/0257925 A1 Aug. 18, 2022

(30) Foreign Application Priority Data

Jun. 26, 2019 (AU) ................................ 2019902232

(51) Int. Cl.
*A61N 1/04* (2006.01)
*A61N 1/05* (2006.01)
(Continued)

(52) U.S. Cl.
CPC ......... *A61N 1/0456* (2013.01); *A61N 1/0541* (2013.01); *A61N 1/36038* (2017.08);
(Continued)

(58) Field of Classification Search
CPC ....... A61N 1/0456; A61N 5/06; A61N 5/0622
See application file for complete search history.

(56) References Cited

U.S. PATENT DOCUMENTS 7,883,536 B1 2/2011 Bendett et al.
8,160,696 B2 4/2012 Bendett et al.
(Continued)

FOREIGN PATENT DOCUMENTS

AU 2011323235 A1 * 5/2013 ............. A61P 25/36
JP 2015-509498 A 3/2015
(Continued)

OTHER PUBLICATIONS

International Search Report issued in PCT Patent Application No. PCT/AU2020/050653 mailed on Aug. 28, 2020.
(Continued)

*Primary Examiner* — Carl H Layno
*Assistant Examiner* — Maria Catherine Anthony
(74) *Attorney, Agent, or Firm* — MARSHALL, GERSTEIN & BORUN LLP

(57) ABSTRACT

Disclosed is a method for stimulating neural tissue, where the neural tissue includes one or more neurons genetically modified to express a light-sensitive protein. The method comprises applying a light stimulus and an electrical stimulus to the neural tissue, thereby triggering membrane depolarisation in at least one of the neurons. Also disclosed is an apparatus for applying the disclosed method. The apparatus includes a light-stimulation device for selectively applying a light stimulus and an electrical-stimulation device for selectively applying an electrical stimulus to the neural tissue.

18 Claims, 17 Drawing Sheets

(51) Int. Cl.
*A61N 1/36* (2006.01)
*A61N 5/06* (2006.01)

(52) U.S. Cl.
CPC ............. *A61N 5/06* (2013.01); *A61N 5/0603* (2013.01); *A61N 5/0622* (2013.01); *A61N 2005/0605* (2013.01); *A61N 2005/0651* (2013.01); *A61N 2005/0662* (2013.01)

(56) References Cited

U.S. PATENT DOCUMENTS

| | | | | |
|---|---|---|---|---|
| 8,926,959 | B2 | 1/2015 | Deisseroth et al. | |
| 8,936,630 | B2 | 1/2015 | Denison et al. | |
| 2010/0114190 | A1 | 5/2010 | Bendett et al. | |
| 2010/0174329 | A1 | 7/2010 | Dadd et al. | |
| 2010/0174330 | A1* | 7/2010 | Dadd | A61N 5/0622 607/3 |
| 2011/0125077 | A1 | 5/2011 | Denison et al. | |
| 2011/0172725 | A1* | 7/2011 | Wells | A61N 1/36017 607/3 |
| 2012/0197374 | A1 | 8/2012 | Vogt et al. | |
| 2015/0289778 | A1 | 10/2015 | Ohl et al. | |
| 2016/0030765 | A1* | 2/2016 | Towne | A61B 18/18 607/88 |
| 2017/0225009 | A1 | 8/2017 | Delp et al. | |

FOREIGN PATENT DOCUMENTS

| | | | |
|---|---|---|---|
| JP | 2016-509487 | A | 3/2016 |
| WO | WO-2010/040142 | A1 | 4/2010 |
| WO | WO-2017/180809 | A1 | 10/2017 |
| WO | WO-2019014680 | A1 | 1/2019 |

OTHER PUBLICATIONS

Written Opinion issued in PCT Patent Application No. PCT/US2020/050653 mailed on Aug. 28, 2020.

* cited by examiner

COMBINED LIGHT AND ELECTRICAL STIMULATION OF LIGHT-SENSITIVE NEURAL TISSUE

CROSS-REFERENCE TO RELATED APPLICATION

This application claims priority to Australian provisional patent application no. 2019902232, filed 26 Jun. 2019, the entire contents of which is incorporated herein by reference.

TECHNICAL FIELD

The present disclosure relates generally to stimulation of neural tissue, and particularly to a method and apparatus for stimulation of neurons genetically modified to express a light-sensitive protein.

BACKGROUND

Stimulation of neural tissue, also known as neuromodulation, provides a means of intervening in the operation of the nervous system. Neuromodulation devices (such as cochlear implants or pacemakers) commonly use electrical stimuli to trigger action potentials in neurons of target neural tissue. However, the need for improvements in spatial selectivity and reduced invasiveness has driven growing interest in other methods of neural modulation, such as optogenetics.

Optogenetics involves genetic engineering of neurons to express light-sensitive ion channels in the plasma membrane of the neuron, such that exposure to light (or certain wavelengths of light) may trigger membrane depolarisation in target neurons.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

According to one aspect, the present disclosure provides a method for stimulating neural tissue, the neural tissue including at least one neuron genetically modified to express a light-sensitive protein, the method comprising:

applying a light stimulus to the neural tissue; and applying an electrical stimulus to the neural tissue thereby triggering membrane depolarisation in one or more neurons of the neural tissue.

Since both a light stimulus and an electrical stimulus is applied to the neural tissue, the disclosed method should be considered to provide combined electrical and light stimulation or "co-stimulation" of the neural tissue (also described herein as "hybrid stimulation" of the neural tissue).

In some embodiments, the membrane depolarisation comprises an action potential. In other embodiments the membrane depolarisation comprises a sub-threshold depolarisation event. A sub-threshold depolarisation event may "prime" or render the neural tissue more easily excitable in response to further stimuli.

A power level of the light stimulus may be below a threshold power level to trigger an action potential in the at least one neuron in the absence of the electrical stimulus (that is, with light-only stimulation). Similarly, a power level of the electrical stimulus may be less than a threshold power level to trigger an action potential in the at least one neuron in the absence of the light stimulus (that is, with electrical-only stimulation).

As used herein, when referring to stimulation of tissue in-vitro, the threshold light power level (also referenced herein as 100% light power level) is defined as the light power level of the light stimulus that will result in a 0.5 probability (i.e. a 1 in 2 chance) of evoking an action potential in the at least one neuron in response to the light stimulus, in the absence of any other stimulus. Similarly, for stimulation of tissue in-vitro, the threshold electrical power level (also referenced herein as 100% electrical power level) is defined as the electrical power level of electrical stimulus that will result in a 0.5 probability (i.e. a 1 in 2 chance) of evoking of an action potential in the at least one neuron in response to the electrical stimulus, in the absence of any other stimulus.

As used herein, when referring to stimulation of tissue in-vivo, the threshold light power level (100% light power level) is defined as light power level of the light stimulus that will result in a 30% increase in neuron firing rate between a spontaneous firing rate and a maximum firing rate. Similarly, for stimulation of tissue in-vivo, the threshold electrical power level (100% electrical power level) is defined as the electrical power level of electrical stimulus that will result in a 30% increase in neuron firing rate between a spontaneous firing rate and a maximum firing rate.

Power levels below or above the threshold power levels, as defined above, are considered "subthreshold" or "suprathreshold", respectively, and may be expressed as a percentage of the light or electrical threshold power level. It will be appreciated that the threshold power level may vary depending on the selected duration of the light or electrical stimuli. In some embodiments, the method may further comprise determining the threshold light power level and/or the threshold electrical power level prior to applying the light stimulus and applying the electrical stimulus.

In some embodiments, the power level of the light stimulus is subthreshold and the power level of the electrical stimulus is suprathreshold. In some embodiments, the power level of the light stimulus is suprathreshold and the power level of the electrical stimulus is subthreshold. In some embodiments, the power level of the light stimulus is subthreshold and the power level of the electrical stimulus is subthreshold. In some embodiments, the power level of the light stimulus is suprathreshold and the power level of the electrical stimulus is suprathreshold.

In some embodiments, when the power level of the light stimulus is subthreshold, the power level of the light stimulus may be between about 5% to 95% of the light threshold power level. For example, the power level of the light stimulus may be about 5%, 10%, 20%, 30%, 40%, 50%, 60%, 70%, 80%, 90%, 95% of the light threshold power level or otherwise.

In some embodiments, when the power level of the electrical stimulus is subthreshold, the power level of the electrical stimulus may be between about 5% to 95% of the electrical threshold power level. For example, the power level of the electrical stimulus may be about 5%, 10%, 20%, 30%, 40%, 50%, 60%, 70%, 80%, 90%, 95% of the electrical threshold power level or otherwise.

In some embodiments, the combined percentages of the threshold power levels of the light stimulus and the electrical stimulus may be less than 100%. As one example, the light stimulus may be 40% of the threshold light power level and the electrical stimulus may be 40% of threshold electrical power level (providing a combined percentage in this example of 40%+40%=80%). It will be appreciated that various combinations of percentages may be used to elicit membrane depolarisation in response to the co-stimulation (combined electrical and light) stimulus. In other embodiments, the combined percentages of the threshold power levels of the light and electrical stimuli may be greater than 100%.

By utilising subthreshold power levels for both the light and electrical stimuli, the disclosed method may reduce the power requirements for artificial stimulation of neurons, resulting in increased energy efficiency of neuromodulation compared to electrical-only or light-only stimulation. Further, reduction of the stimulus power, or stimulus intensity, may reduce unwanted side-effects from light or electrical stimulation of the neural tissue compared to electrical-only or light-only stimulation. Unwanted side-effects may include light toxicity or electrical damage to the stimulated cells. For example, temperature or heat build-up, either through light absorption or from a light source (for example, embedded LEDs or batteries), may cause cell damage. Further, the ability to excite neurons using a low (subthreshold) power level of the electrical stimulus may enable design modifications to known neuromodulation devices. For example, the ability to stimulate using a lower electrical power level may ameliorate design constraints relating to charge density on electrodes, potentially enabling use of electrodes having a smaller effective electrode area.

In embodiments where the power level of the electrical stimulus is subthreshold, the method may result in reduced spread of the electrical current within the stimulated neural tissues, thus allowing improvement in the spatial resolution of the applied stimulation, providing for more precise activation of target neurons. Further, a subthreshold power electrical stimulus may generate a reduced stimulation artefact compared to conventional electrical-only stimulation. This may improve the quality of recording of the neural response to the stimulation.

Moreover, the combined electrical and light stimulation of light-sensitive neural tissue may provide improved temporal accuracy, allowing neurons to be stimulated at faster rates compared to light-only stimulation. This may be particularly advantageous in applications such as cochlear implant systems where fast firing rates are used to represent sound information. The method may enable stimulation of light-sensitive neural tissue at higher frequencies than light-only stimulation, without the need to re-engineer the light sensitive proteins to have faster kinetic properties. Thus, the present method may result in higher spatial and/or temporal precision.

The duration of the applied light stimulus may be greater than about 0.1 ms, 0.5 ms, 1 ms or otherwise. The duration of the applied light stimulus may be less than about 100 ms, less than about 50 ms, less than about 20 ms or otherwise. For example, the duration of the light stimulus may be between about 0.1 to 100 ms, 0.1 to 50 ms, 0.1 to 20 ms, 0.5 to 100 ms, 0.5 to 50 ms, 0.5 to 20, 1 to 100 ms, 1 to 50 ms, 1 to 20 ms or otherwise. For example, the duration of the light stimulus may be about 0.1 ms, 0.2 ms, 0.5 ms, 1 ms, 2 ms, 4 ms, 6 ms, 8 ms, 10 ms, 12 ms, 14 ms, 16 ms, 18 ms, 20 ms, 30 ms, 40 ms, 50 ms, 100 ms or otherwise. The duration of the light stimulus may be configured to correspond to a period required for a stimulated neuron to reach a desired (or a peak) level of excitability. It will be appreciated that the duration of the light stimulus required to reach the desired level of excitability may be reduced for a light stimulus having a higher power level. A period of enhanced excitability (also referred to herein as "facilitation period") of the neuron may persist after cessation of the applying of the light stimulus. For example, in embodiments utilising certain opsins such as step function opsins (SFOs) or stabilised step function opsins (SSFOs), the period of enhanced excitability may persist for seconds or minutes after the cessation of the application of the light stimulus.

The applying of the electrical stimulus may start at the same time as, or at a predetermined delay time after, the start of the applying of the light stimulus. The predetermined time delay may be between about 0.1 ms to about 60 ms or otherwise. For example, the predetermined delay time may be about 0.1 ms, 0.2 ms, 0.5 ms, 1 ms, 5 ms, 10 ms, 15 ms, 20 ms, 25 ms, 30 ms, 40 ms, 50 ms, 60 ms, or more. In some embodiments, the predetermined delay time may be selected such that the electrical stimulus starts substantially within a period in which a stimulated neuron is in a state of enhanced excitability resulting from the light stimulus. In some embodiments, such as embodiments employing step-function opsins, the state of enhanced excitability may persist for a relatively long period of time, in the order of seconds or minutes after cessation of the applying of the light stimulus. In some embodiments, the predetermined time delay may be up to 30 minutes. For example, the predetermined time delay may be about 0.1 s, 0.2 s, 0.3 s, 0.4 s, 0.5 s, 0.6 s, 0.8 s, 1 s, 2 s, 3 s, 4 s, 5 s, 10 s, 15 s, 20 s, 30 s, 45 s, 1 minute, 2 minutes, 5 minutes, 10 minutes, 15 minutes, 20 minutes, 25 minutes, 30 minutes or more. In some alternative embodiments, the electrical stimulus may start before the light stimulus.

It may be possible to deliver multiple electrical pulses within a period of enhanced excitability of the neuron resulting from the light stimulus. In some embodiments, the electrical stimulus may be applied as a series of pulses, or as a pulse train. In such embodiments, one or more of the electrical pulses may occur at a predetermined time delay after or before the start of the applying of the light stimulus. In some embodiments, the electrical stimulus may be applied substantially continuously, for example, as a substantially continuous series of pulses. In some embodiments, the electrical pulses may be applied at a predetermined pulse frequency. For example, the predetermined pulse frequency may be between about 5 Hz to about 5 kHz or more. For example, the frequency may be about, or may be greater than, 5 Hz, 10 Hz, 20 Hz, 30 Hz, 40 Hz, 50 Hz, 60 Hz, 70 Hz, 80 Hz, 90 Hz, 100 Hz, 150 Hz, 200 Hz, 300 Hz, 400 Hz, 500 Hz, 600 Hz, 700 Hz, 800 Hz, 900 Hz, 1 kHz, 2 kHz, 3 kHz, 4 kHz, 5 kHz or more. Combined light and electrical stimulation carried out according to the present disclosure may enable triggering of membrane depolarisation using higher pulse frequencies than is possible with light stimulation alone.

In some embodiments, the predetermined delay time is greater than a duration of the applying of the light stimulus, such that the applying of the electrical stimulus starts after cessation of the applying of the light stimulus. In other embodiments, the predetermined delay time is less than a duration of the applying of the light stimulus, such that the applying of the electrical stimulus starts before cessation of the applying of the light stimulus.

The "applying" may be considered to take place while a light or electrical stimulation element, that delivers the light or electrical stimulus signals or pulses, respectively, to neural tissue, is in an active or "on" state. As herein described, the start, beginning or onset of the applied electrical or light stimulus is defined as the leading-edge half maximum of the associated stimulus signal or pulse. Similarly, the end or cessation of the applied electrical or light stimulus is defined as the trailing-edge half maximum of the associated stimulus signal or pulse. As outlined above, a period of enhanced excitability of the neuron as a result of the applying of the light stimulus may persist after cessation of the applying of the light stimulus.

Applying the electrical stimulus to coincide with a period of enhanced excitability after cessation of the applying of the light stimulus may further reduce the risk of unwanted side effects of light stimulation, such as light-toxicity, as the light stimulus may not need to be applied at all times for effective stimulation of the neural tissue to generate action potentials. Further, increased energy efficiency may be achieved in such embodiments, as the light stimulus and electrical stimulus need not be applied simultaneously, which may reduce the instantaneous and/or overall power requirements for stimulation.

Related to this, according to one aspect, there is provided a method for stimulating neural tissue, the tissue including one or more neurons genetically modified to express a light-sensitive protein, the method comprising:

applying a light stimulus to the neural tissue; and applying an electrical stimulus to the neural tissue;

thereby triggering membrane depolarisation in at least one of the neurons, wherein applying of the electrical stimulus starts after cessation of the applying of the light stimulus.

There may be a gap in time between the cessation of the applying of the light stimulus and the start of the applying of the electrical stimulus. The applying of the electrical stimulus may start between about 0.1 ms to about 60 ms or otherwise, after cessation of the applying of the light stimulus. For example, the applying of the electrical stimulus may start about 0.1 ms, 0.2 ms, 0.5 ms, 1 ms, 5 ms, 10 ms, 15 ms, 20 ms, 25 ms, 30 ms, 40 ms, 50 ms, 60 ms or more, after cessation of the applying of the light stimulus. In some embodiments, the time after cessation may be selected such that the electrical stimulus starts substantially within a period in which a stimulated neuron is in a state of enhanced excitability resulting from the light stimulus. In some embodiments, such as embodiments employing step-function opsins, the state of enhanced excitability may persist for a relatively long period of time, in the order of seconds or minutes after cessation of the applying of the light stimulus. In some embodiments, the applying of the electrical stimulus may start up to 30 minutes after the cessation of the applying of the light stimulus, e.g., about 0.1 s, 0.2 s, 0.3 s, 0.4 s, 0.5 s, 0.6 s, 0.8 s, 1 s, 2 s, 3 s, 4 s, 5 s, 10 s, 15 s, 20 s, 30 s, 45 s, 1 minute, 2 minutes, 5 minutes, 10 minutes, 15 minutes, 20 minutes, 25 minutes, 30 minutes or more, after the cessation of the applying of the light stimulus.

In some embodiments, the light stimulus may be applied as a series of pulses or as a pulse train to maintain excitability of at least one target neuron. In some embodiments, the light stimulus may be substantially continuous.

The light stimulus may comprise light having a wavelength in the UV, visible or infrared spectrum. The light stimulus may comprise light having a wavelength of between about 300 nm to about 2000 nm. Nevertheless, in some embodiments it may be preferable that the light stimulus comprises light in the visible light spectrum, and may therefore exclude infrared light or ultraviolet light, for example. For example, the light stimulus may comprise light having wavelengths between about 380 nm to about 740 nm. In some embodiments, the light stimulus may comprise light having wavelengths between about 450 nm to about 600 nm.

The wavelength of the light may be selected to correspond to one or more wavelength sensitivities of the light-sensitive protein of the genetically modified neurons. In some embodiments, the light stimulus may comprise multiple discrete wavelengths of light. In some embodiments, the light stimulus may comprise light having a continuous range of wavelengths across a predetermined band. In other embodiments, the light stimulus may comprise light of a single discrete wavelength.

By relying on light-sensitive, optogenetically modified tissue and particularly through use of light having wavelengths that can be within the visible spectrum, the present techniques may be considerably different from infrared neural stimulation techniques, which rely on a thermal mechanism of activation of neural tissue, whereby a rapid change in temperature triggers action potentials in target neurons.

According to one aspect, the present disclosure provides an apparatus configured to perform the method of the preceding aspect. The apparatus may comprise a light stimulation device for selectively applying the light stimulus; and an electrical stimulation device for selectively applying the electrical stimulus.

Related to this, according to one aspect, the present disclosure provides an apparatus configured to stimulate neural tissue, the tissue including one or more neurons genetically modified to express a light-sensitive protein, the apparatus comprising:

a light stimulation device for selectively applying a light stimulus to the neural tissue; and an electrical stimulation device for selectively applying an electrical stimulus to the neural tissue;

thereby triggering membrane depolarisation in at least one of the neurons.

The apparatus may be at least partially implantable. The apparatus may comprise an implantable housing or substrate that supports at least part of the light stimulation device and/or at least part of the electrical stimulation device. The apparatus may be configured for partial implantation in a human or animal patient for diagnosis and/or treatment purposes.

The light stimulation device may comprise a light energy source and at least one light stimulation element for applying light energy from the light energy source to the neural tissue. At least the light stimulation element may be implantable. For example, at least the light stimulation element and optionally both the light stimulation element and the light energy source may be supported by the implantable housing or substrate.

Similarly, the electrical stimulation device may comprise an electrical energy source and at least one electrical stimulation element for applying the electrical energy to the neural tissue. At least the electrical stimulation element may be implantable. For example, at least the electrical stimulation element and optionally both the electrical stimulation element and the electrical energy source may be supported by the implantable housing or substrate.

In some embodiments, the housing or substrate may include a neural interface portion that may be configured to be positioned in proximity to, or in direct contact with, the neural tissue to be stimulated. The electrical stimulation element and the light stimulation element may be positioned on or in the neural interface portion, or otherwise supported by the neural interface portion. The neural interface portion may be a surface of the substrate or housing that faces and/or contacts the neural tissue to be stimulated. At least the neural interface portion of the housing or substrate may be flexible, and/or pre-formed with a shape, such that it can substantially conform to the shape of neural tissue to be stimulated.

In some embodiments, the apparatus further comprises a system controller for controlling the application of the light stimulus and the electrical stimulus. For example, the system controller may be configured for selectively triggering the application of the light stimulus and the electrical stimulus. The system controller may be configured to trigger application of the electrical stimulus a predetermined delay time after triggering application of the light stimulus. Additionally or alternatively, the system controller may be configured to control a duration and/or a power level of the light and electrical stimuli.

In some embodiments, the apparatus further comprises a recording device configured to detect neural activity. The recording device may comprise recording electrodes connected to an oscilloscope, controller, computer interface or other signal processing apparatus, for example, neural response telemetry apparatus or auditory brainstem response apparatus. In some embodiments, the recording electrodes of the recording device may comprise electrical stimulation elements of the electrical stimulation device. In such embodiments, the electrical stimulation elements may be selectively operable as stimulating or recording electrodes. Alternatively, the recording device may be a calcium imaging apparatus. The recording device may be configured to detect, record and/or monitor a response of the neural tissue to the light and electrical stimuli. For example, the recording device may detect a change in membrane potential and/or action potentials generated in response to the electrical and/or light stimuli. Additionally or alternatively, the recording device may be configured to measure parameters associated with the electrical and/or light stimulation including the duration or power level of the stimulus or the delay time between stimuli. In some embodiments, the recording device may enable closed-loop control of the apparatus.

The disclosed method and apparatus may be used to stimulate neural tissue to alter the activity of neurons at selected neurological sites in the body (for example, of a human patient). The method and apparatus may be used as part of a neuroprosthetic device to supplement or replace the normal functioning of a patient's nervous system. For example, the method and apparatus may be used as part of a cochlear implant system to trigger action potentials in the auditory nerve and provide or augment hearing sensation. In general, the method and apparatus may be useful in various neuromodulation applications including but not limited to auditory nerve stimulation, auditory brainstem stimulation, spinal cord stimulation, deep brain stimulation, functional electrical stimulation, brain-computer interfaces, peripheral nerve stimulation, retinal stimulation or other nerve stimulation applications. Such applications may be useful, for example, in detection and/or treatment of hearing loss, epilepsy, depression, motor neurone diseases and other therapeutic applications.

Throughout the specification and claims the word "comprise", or variations such as "comprises" or "comprising", will be understood to imply the inclusion of a stated element, integer or step, or group of elements, integers or steps, but not the exclusion of any other element, integer or step, or group of elements, integers or steps.

DESCRIPTION OF EMBODIMENTS

Methods for stimulating neural tissue according to embodiments of the present disclosure are now described.

Figure 1:
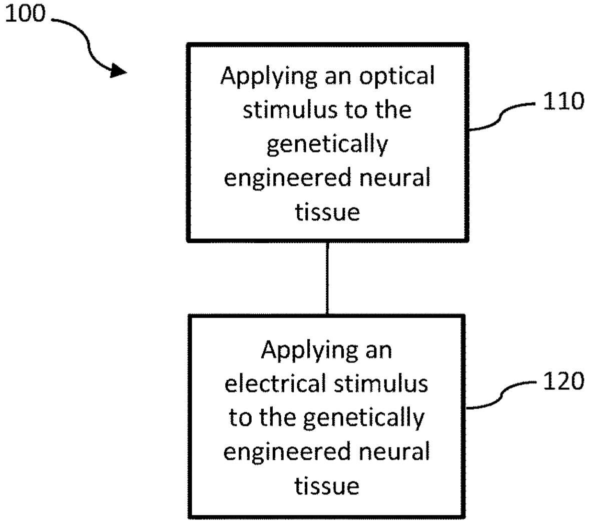
FIG. 1 shows a flowchart of steps carried out in a method of stimulating neural tissue, the tissue including one or more neurons genetically modified to express a light-sensitive protein, according to an embodiment of the present disclosure.

Referring to flowchart 100 of FIG. 1, a method for stimulating neural tissue according to an embodiment of the present disclosure is disclosed, the tissue including one or more neurons genetically modified to express a light-sensitive protein. The method comprises applying a light stimulus 110 to the neural tissue and applying an electrical stimulus 120 to the neural tissue, thereby triggering membrane depolarisation in at least one of the neurons. The relative positions of the method steps as depicted in flowchart 100 should not be interpreted as limiting those steps to being performed in any particular order.

Figure 2:
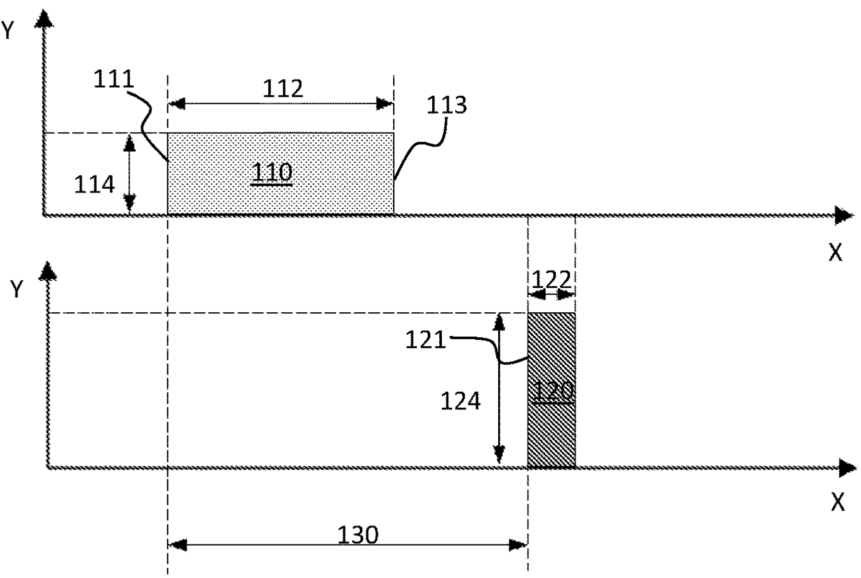
FIG. 2 shows a graphical representation of the light stimulus and electrical stimulus of the method of FIG. 1.

In FIG. 2, the applying of the light stimulus 110 and the applying of the electrical stimulus 120 are each represented graphically, where the X-axes represent time and the Y-axes represent stimulus power. The light stimulus 110 has a duration 112 and a light power level 114. Similarly, the electrical stimulus 120, has a duration 122 and an electrical power level 124. It will be appreciated that the amount of energy delivered to the neural tissue as a result of applying the light stimulus 110 and applying the electrical stimulus 120 may vary depending on the selected duration and power level of the respective stimuli.

The start 111 of the applying of the light stimulus 110 and the start 121 of the applying of the electrical stimulus 120 are separated by a predetermined delay time 130, such that the applying of the electrical stimulus 120 starts after the start of the applying of the light stimulus 110. In the illustrated embodiment, the predetermined delay time 130 is greater than the duration 112 of the light stimulus 110. As a result, the start 121 of applying of the electrical stimulus 120 occurs after the cessation 113 of the applying of the light stimulus 110, there being a gap in time between the cessation 113 of the applying of the light stimulus 110 and the start of the applying of the electrical stimulus 120. It will be appreciated, however that the predetermined delay time 130 may be less than the duration 112 of the light stimulus 110, such that the start 121 of the applying of the electrical stimulus 120 occurs before the cessation 113 of the applying of the light stimulus 110 (that is, such that the applying of the electrical stimulus at least partially overlaps with the applying of the light stimulus 110). In some embodiments, the predetermined delay time 130 may be configured such that the start 121 of the applying of the electrical stimulus 120 coincides with the end 113 of the applying of the light stimulus 110.

In some embodiments, the predetermined time delay 130 may be configured to correspond to a period required for a stimulated genetically modified neuron to reach a peak level of excitability in response to the light stimulus 110. As shown in the example of FIG. 6D, discussed in more detail below, the firing probability, AP/pulse, of a neuron (that is, the probability of achieving an action potential at the neuron in response to applying of the electrical stimulus) can be strongly correlated with the change in membrane potential, $\Delta V_m$, of the neuron as a result of the applying of the light stimulus 110, such that the chance of generating an action potential in the neuron in response to applying of the electrical stimulus 120 is maximised when the applying of the electrical stimulus 120 is started towards the end 113 or after cessation of the applying of the light stimulus 110.

In some embodiments, the electrical stimulus may be applied as a series of electrical pulses. In some embodiments, the electrical pulses may be applied at a predetermined pulse frequency, for example, between about 5 Hz to about 5 kHz or more. FIGS. 8A to 8E, for example, show experimental data from stimulation using an electrical stimuli comprising pulse trains at various predetermined pulse frequencies. The pulse frequency may be selected according to the nerve stimulation application at hand. For example, relatively low pulse frequencies, such as about 130 Hz, may be used for applications such as deep-brain stimulation, whereas relatively high pulse frequencies, up to 5 kHz or more, may be used for applications such as auditory nerve stimulation to produce a hearing percept. Combined light and electrical stimulation that is carried out according to the present disclosure may enable triggering of membrane depolarisation using higher pulse frequencies than is possible with light stimulation alone.

Figure 3A:
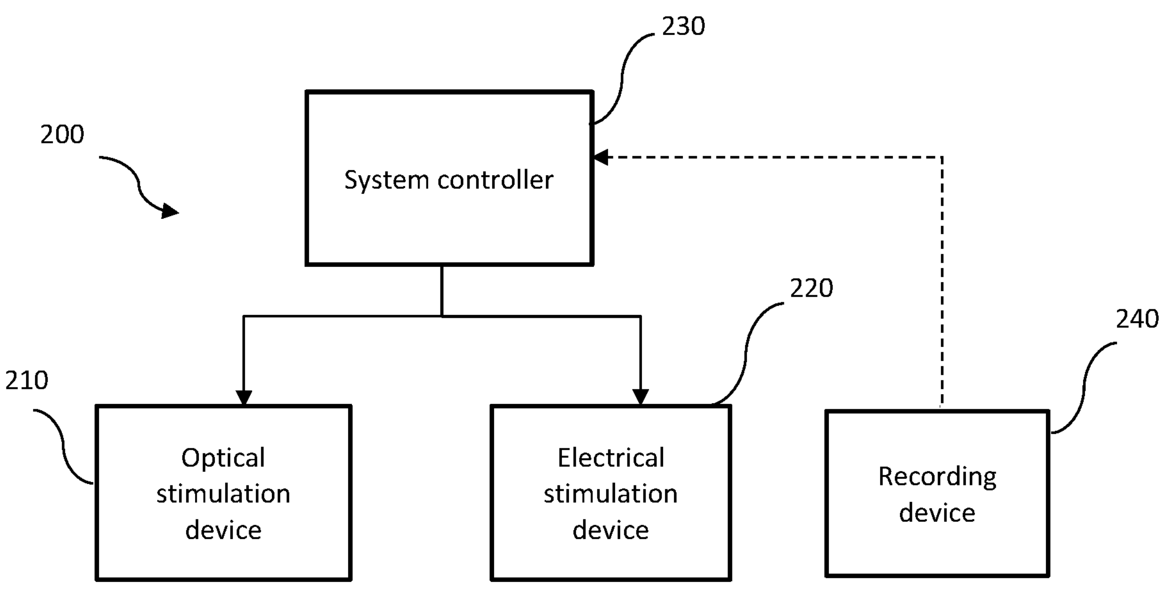
FIG. 3A shows a system diagram of apparatus according to an embodiment of the present disclosure configured to perform the method of FIG. 1.

An apparatus 200 suitable for use in methods described herein is shown in system diagram of FIG. 3. The apparatus 200 is configured to stimulate neural tissue, the tissue including one or more neurons genetically modified to express a light-sensitive protein. The apparatus 200 comprises a light stimulation device 210 for selectively applying a light stimulus to the neural tissue and an electrical stimulation device 220 for selectively applying an electrical stimulus to the neural tissue, thereby triggering membrane depolarisation in at least one of the neurons.

Optionally, the apparatus 200 comprises a system controller 230 for controlling the application of the light stimulus and the electrical stimulus. The system controller 230 may selectively trigger the applying of the light stimulus 110 and selectively trigger the applying of the electrical stimulus 120. The system controller 230 may be configured to trigger the applying of the light and electrical stimuli in sequence such that the applying of the electrical stimulus is triggered a predetermined delay time 130 after the applying of the light stimulus. The system controller 230 may be configured to control various parameters of the light stimulus 110 and the electrical stimulus 120, including the duration 112, 122 and power levels 114, 124 of the electrical and light stimuli or otherwise.

Figure 3B:
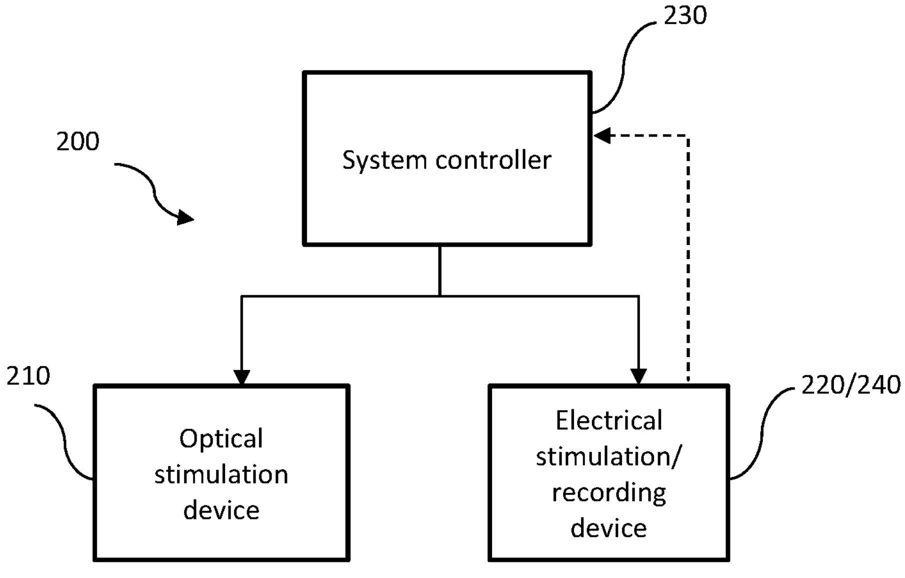
FIG. 3B shows a system diagram of apparatus according to another embodiment of the present disclosure configured to perform the method of FIG. 1.

The apparatus 200 optionally comprises a recording device 240 which may include, for example, recording electrodes connected to an oscilloscope, computer interface, neural response telemetry system or other signal processing device. The recording device 240 may be configured to monitor a response of the stimulated neural tissue to the applied electrical and/or light stimuli. Additionally or alternatively, the recording device 240 may be configured to monitor parameters of the applied light and/or electrical stimuli including duration, power levels, and time delay. As indicated by the dashed line in FIG. 3A the recording device 240 may be associated with the system controller 230. Alternatively, the recording device 240 may be integral with the electrical stimulation device 220, as shown in FIG. 3B. For example, the system controller 240 may be configured to automatically adjust parameters of the electrical and light stimuli 110, 120 based on data received from the recording device 240, thereby to provide closed-loop control of the apparatus 200.

Figure 4A:
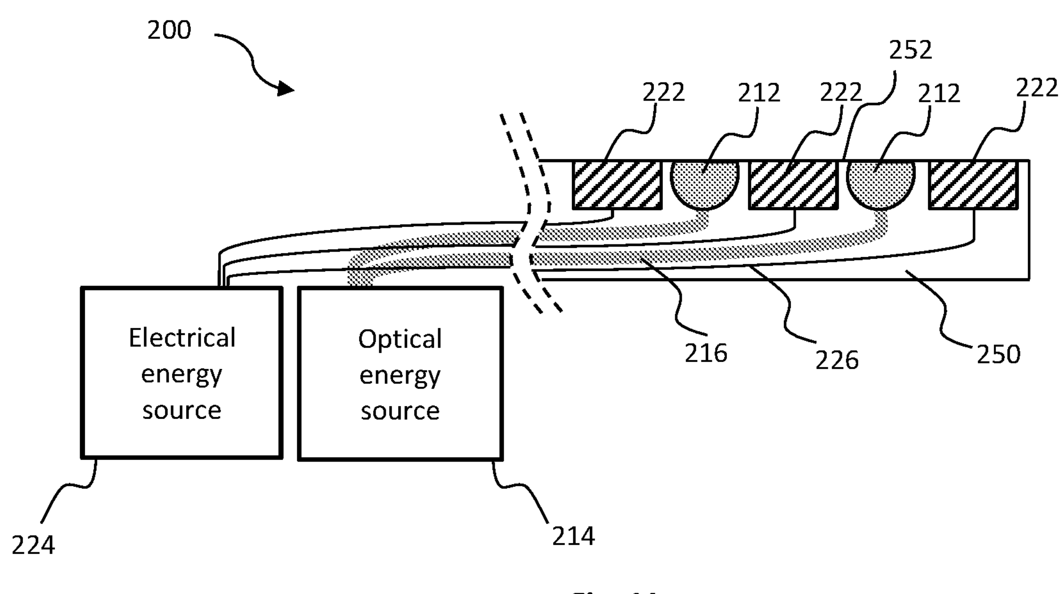
FIGS. 4A and 4B show schematic representations of apparatus according to embodiments of the present disclosure.

Referring to FIG. 4A, the apparatus may include an implantable substrate 250 that partially supports the light stimulation device 210 and the electrical stimulation device 220. The substrate 250 includes a neural interface portion 252 configured to be positioned in proximity to (or in direct contact with) the neural tissue to be stimulated. For example, as shown in FIG. 4A, the neural interface portion 252 may be a surface of the substrate 250 that faces and/or contacts the neural tissue to be stimulated. The neural interface portion 252 may be flexible, and/or pre-formed with a shape, such that it can substantially conform to the shape of neural tissue to be stimulated.

In this embodiment, the light stimulation device 210 comprises at least one light energy source 214 connected to a plurality of light stimulation elements 212. The light energy source 214 may be selected from the group including laser, light-emitting diode (LED) and laser diode or other suitable light energy source.

The electrical stimulation device similarly comprises at least one electrical energy source 224 connected by conductors 226 to a plurality of electrical stimulation elements. The electrical energy source 224 may comprise an electrical signal generator or other suitable electrical energy source. The electrical stimulation elements 222 may be in the form of electrodes 222 for applying the electrical energy to the neural tissue.

In this embodiment, the plurality of light stimulation elements 212 and the plurality of electrical stimulation elements 222 are positioned in an array, each spaced apart along the neural interface portion 252 for applying the light and electrical stimuli 110, 120 to the neural tissue.

In some embodiments, light energy is transmitted from the light energy source 214 to the light stimulation elements 212 by light transmitters 216. The light transmitters may be optical fibres, waveguides (or other suitable light transmission means). In some embodiments, the light stimulation elements 212 further comprise refractors and/or reflectors for more directing the light energy to the neural tissue.

In alternative embodiments, the light energy may be generated locally to the neural interface portion 252 for directly irradiating the neural tissue (for example, the light energy source 214 may be integral with the light-stimulation element 212, thus negating the need for a light transmitter). For example, the light stimulation device 210 may comprise one or more lasers, micro-LEDs or other suitable light energy sources supported on the implantable substrate 250.

Figure 4B:
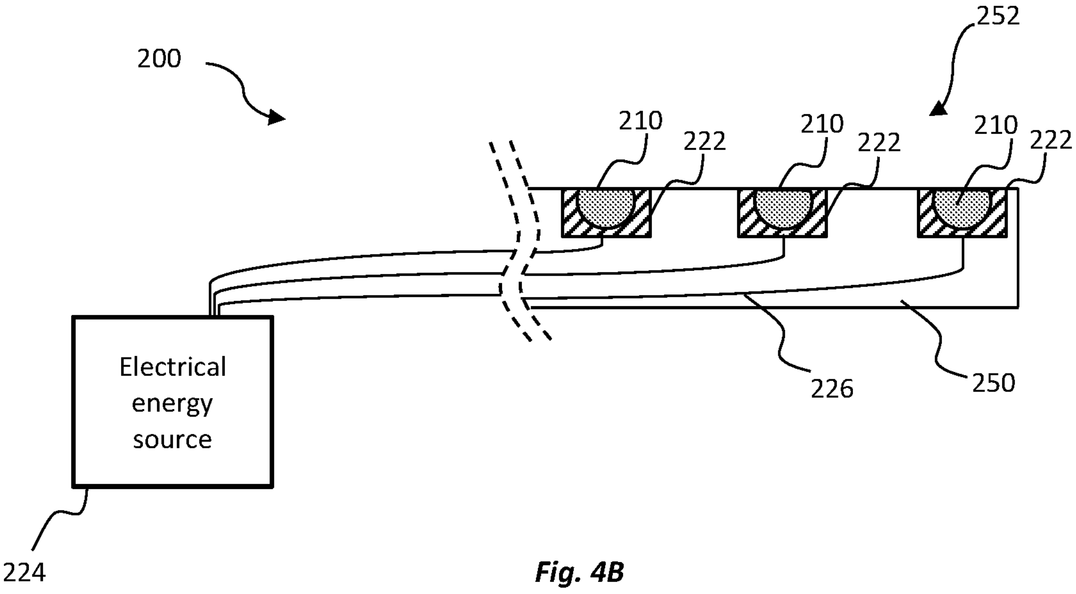

In the embodiment shown in FIG. 4A, the light stimulating elements 212 and the electrical stimulating elements 222 are discretely located. However, in alternative embodiments, the light and electrical components may be at least partially combined. For example, light stimulating devices 210 may be provided that are wholly or partially integrated with the electrical stimulation elements 222. For example, referring to the embodiment illustrated in FIG. 4B, the neural interface portion 252 comprises a plurality of electrical stimulating elements in the form of electrodes 222 having an integral light stimulating device 210 in the form of an embedded micro-LED. As another example, although not illustrated, light stimulating elements may be provided by ends of optical fibres (or optical fibre bundles), and electrical stimulating elements may be provided by conductive outer coatings of the optical fibres or optical fibre bundles.

Although the illustrated embodiments show one-dimensional, linear arrays of electrical and light stimulation elements, in any of the above described embodiments the array(s) may be two-dimensional or three-dimensional.

The term "genetically modified" is used in the context of the present disclosure refers to a permanent or transient genetic change induced in a cell following introduction into the cell of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. In the context of the present disclosure, the introduced nucleic acid encodes a light sensitive protein.

Various suitable method(s) of genetic modification are known in the art. For example, expression vectors encoding a light-sensitive protein disclosed herein can be delivered directly to neurons of the central or peripheral nervous system with a needle, catheter, or related device, using neurosurgical techniques known in the art, such as by stereotactic injection (See, e.g., Davidson et al., Nat. Genet., 1993, 3:219-223; and Alisky & Davidson, Hum. Gene Ther., 2000, 11:2315-2329) or fluoroscopy. Other suitable methods of genetic modification include viral infection, transfection, conjugation, protoplast fusion, electroporation, particle gun technology and calcium phosphate precipitation. In an example, genetically modified neurons can be identified using a reporter gene or selectable marker. In another example, genetically modified neurons can be identified based on their expression of a light sensitive protein disclosed herein. For example, levels of nucleic acid encoding the light sensitive protein can be measured using routine amplification based detection methods such as PCR. In other examples, light-sensitive protein levels can be assessed via immunohistochemistry or ELISA based assays.

Various expression vectors may be employed to genetically modify neurons disclosed herein. The term "expression vector" is used in the context of the present disclosure to refer to a genetic construct which is capable of facilitating expression of a nucleic acid in a host cell. An expression vector can exist in the form of an isolated polynucleotide, for example "naked DNA", or can comprise one or more agents which enhance delivery to the host cell, such as a viral capsid and/or envelope, a lipid, or a polymer. Accordingly, examples of expression vectors encompassed by the present disclosure include, without limitation, naked DNA, phage, viruses, nanoparticles such as lipid-based nanoparticles, plasmids, linear DNA, cosmids, episomes, mini-circle DNA (for example, as described in US 2004/0214329), and bacteria. Generally, the expression vector is capable of transforming a neuron host cell and effecting expression of a nucleic acid encoding a light sensitive protein. The selection of expression vector will depend on a variety of factors such as, for example, the host, immunogenicity of the vector, the desired duration of light-sensitive protein production, and the like. In one example, the expression vector is a viral vector. In some examples, the expression vector directs expression of the light sensitive protein in a particular neuronal cell type. Thus, in some examples, the expression vector comprises a cell-type specific promoter. For example, the expression vector can comprise a spiral ganglion neuron cell specific promoter.

Neural tissue comprises neurons and one or more neurons comprising the neural tissue may be genetically modified to express a light-sensitive protein. Accordingly, individual or population(s) of neurons may be stimulated via the methods of the present disclosure. Neurons stimulated via methods disclosed herein are not particularly limited so long as they express a light-sensitive protein. Exemplary neurons include those of the central or peripheral nervous systems. For example, neurons that can be stimulated via methods disclosed herein include sensory neurons, motor neurons, interneurons and neurons in the brain. In an example, neurons stimulated via methods disclosed herein are sensory neurons. In another example, the neurons are motor neurons. In another example, the neurons are interneurons. In another example, the neurons are neurons in the brain. In another example, the neurons are spiral ganglion neurons. In another example, the neurons are retinal neurons.

Light-sensitive proteins encompassed by the present disclosure are not particularly limited so long as they can be stimulated using a method disclosed herein. In an example, suitable proteins are light-responsive channel or pump proteins that locate to the plasma membranes of genetically modified neuronal cells. For example, the light-sensitive protein (for example, an opsin) may act as a light-activated ion transport channel in at least one genetically modified neuron. In an example, the light sensitive protein can be a light-sensitive opsin. Examples of light-sensitive opsins include opsins that induce hyperpolarization in neurons by light and opsins that induce depolarization in neurons by light. Examples of opsins are shown in Table 1 below.

TABLE 1

Example opsins for excitation and modulation across the visible spectrum.

| Opsin Type | Biological Origin | Wavelength Sensitivity | Defined action |
|---|---|---|---|
| VChR1 | *Volvox carteri* | 589 nm utility<br>535 nm max | Excitation (depolarization) |
| DChR | *Dunaliella salina* | 500 nm max | Excitation (depolarization) |
| ChR2 | *Chlamydomonas reinhardtii* | 470 nm max<br>380-405 nm utility | Excitation (depolarization) |
| ChETA | *Chlamydomonas reinhardtii* | 470 nm max<br>380-405 nm utility | Excitation (depolarization) |
| SFO | *Chlamydomonas reinhardtii* | 470 nm max | Excitation (depolarization) |
| | | 530 nm max | Inactivation |
| SSFO | *Chlamydomonas reinhardtii* | 445 nm max | Step-like activation (depolarization) |
| | | 590 nm; 390-400 nm | Inactivation |
| C1V1 | *Volvox carteri* and *Chlamydomonas reinhardtii* | 542 nm max | Excitation (depolarization) |
| C1V1 E122 | *Volvox carteri* and *Chlamydomonas reinhardtii* | 546 nm max | Excitation (depolarization) |
| C1V1 E162 | *Volvox carteri* and *Chlamydomonas reinhardtii* | 542 nm max | Excitation (depolarization) |
| C1V1 E122/E162 | *Volvox carteri* and *Chlamydomonas reinhardtii* | 546 nm max | Excitation (depolarization) |

In an example, the light-sensitive protein is a light-sensitive chloride pump. For example, the protein can be one or more members of the Halorhodopsin family of light-sensitive chloride pumps. In an example, the light-sensitive chloride pump protein is derived from *Natronomonas pharaonis*. In another example, the light-sensitive chloride pump protein is derived from *Halobacterium salinarum*. In another example, the light-sensitive protein is a light-sensitive proton pump. In an example, the light-sensitive proton pump protein is derived from *Guillardia theta*. In another example, the light-sensitive protein is a light-sensitive cation channel. In an example, the light-sensitive cation channel protein is derived from *Chlamydomonas reinhardtii*. In an example, the cation channel protein is capable of mediating a depolarizing current in a genetically modified neuron when the neuron is stimulated via a method disclosed herein. In an example, the light sensitive protein is Channelrhodopsin-2 (ChR2). In another example, the light sensitive protein is ChR2/H134 (ChR2(H134R) carries a single point mutation at position H134). See NCBI accession number AF461397. In another example, the light sensitive protein is derived from *Dunaliella salina*. For example, the light sensitive protein can be a DChR.

Example 1

Cultures of dissociated spiral ganglion neurons (SGNs) were prepared from male and female postnatal day 3-5 transgenic mice expressing ChR2*H134R in SGNs.

For each neuron, the firing threshold (the power level where action potentials (APs) were evoked for at least half of presented stimuli) was determined separately for 3 ms electrical pulses (176±13 pA) and 10 ms optical stimuli (10.3±3.4 mW, measured at the tip of the optical fibre in air). APs were defined as any rapid spike in membrane voltage where instantaneous rate of change exceeded a rate of change threshold. The threshold power was defined as 100% stimulation level, while power levels below or above were denoted "subthreshold" and "suprathreshold" respectively.

Figure 5A:
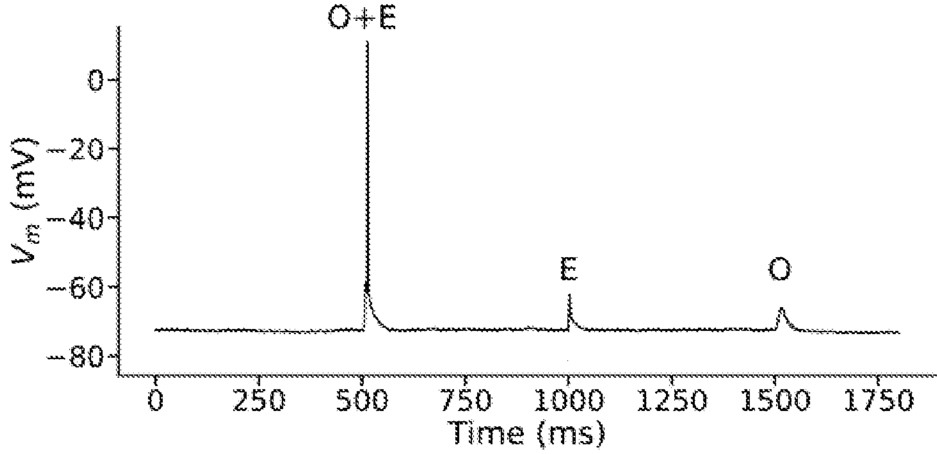
FIG. 5A shows a trace typical of a genetically modified neuron response to electrical-only (E), optical-only (O) and optical and electrical co-stimulation (O+E) with optical and electrical power each at sub-threshold levels.

A stimulation protocol consisting of three sequential pulses was applied: combined optical and electrical (O+E), electrical-only (E) and optical-only (O), with individual power levels set to subthreshold levels. FIG. 5A shows a typical cell response to the stimulation protocol, with the O+E pulse evoking an AP while separate E and O pulses did not.

Figure 5B:
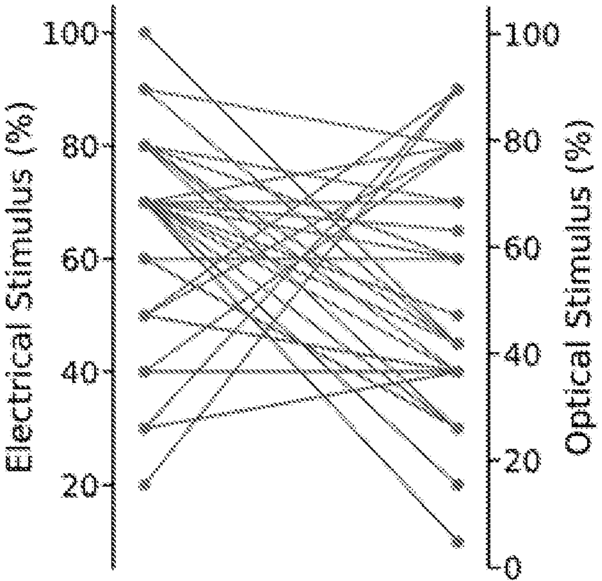
FIG. 5B shows a diagram mapping several combinations of stimulus levels which evoked action potentials during co-stimulation of a neuron.

FIG. 5B shows several combinations of stimulus levels which evoked APs during co-stimulation, indicating that co-stimulation APs can be evoked with either electrical or optical stimulation as the dominant stimuli. For several combinations the sum of the two stimuli was below 100%, for instance 40% electrical and 40% optical.

Figure 5C:
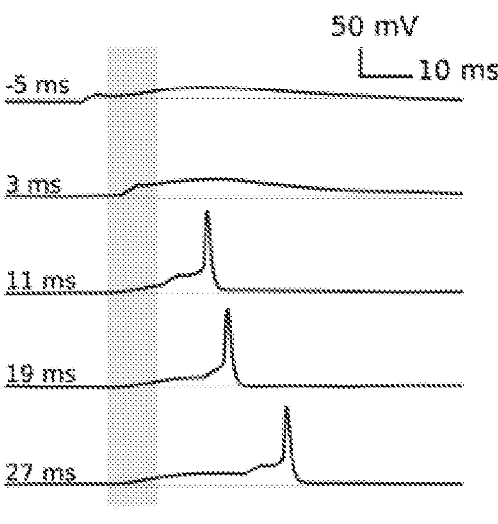
FIGS. 5C, 5D and 5E show traces obtained from optical and electrical co-stimulation at various delays between the two stimuli and at different power levels.
Figure 5D:
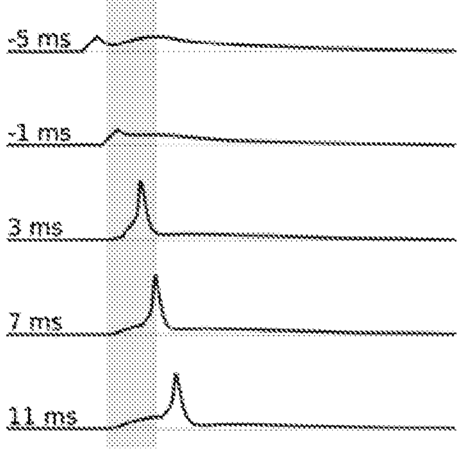
Figure 5E:
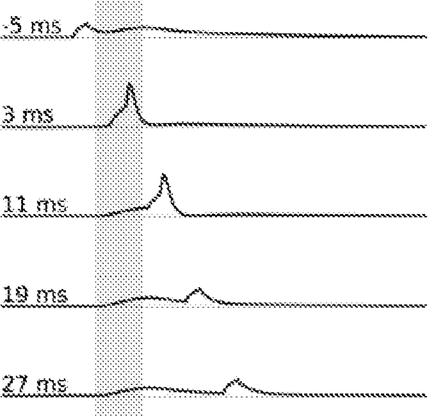

FIGS. 5C, 5D and 5E, show O+E co-stimulation at various delay times between the two stimuli and at different power levels. The power levels represented are: FIG. 5C 40% optical, 40% electrical; FIG. 5D 45% optical, 80% electrical; and FIG. 5E 65% optical and 70% electrical. The shaded area indicates the duration of the optical stimulus. The timing of the onset of electrical stimulus relative to the optical stimulus onset varies, starting at the top line with electrical leading optical by 5 ms. In each subsequent trace the start of the applying of the electrical stimulus is delayed further relative to the start of the applying of the optical stimulus. When the electrical stimulus precedes the optical stimulus, two phases of depolarisation are evident (a sharp electrical depolarisation and a more gradual optical depolarisation) and no AP is elicited. Where the electrical "trigger" pulse occurs, when the membrane is sufficiently depolarised by the optical base, an AP is evoked. These figures reveal a temporal dependency for the co-stimulation effect, as most APs occur later in the optical stimulation period or after the completion of the optical stimuli.

In wild type cells not expressing ChR2, maximum power optical pulses did not elicit membrane depolarisation, and when presented together with electrical stimulation as high as 90% also failed to elicit APs (n=4 cells, data not shown). These results indicate that the presence of ChR2/H134 in the membrane is required to elicit co-stimulation APs, and that simultaneous activation of optogenetic and voltage sensitive ion channels is necessary to evoke APs by combined subthreshold stimuli.

Figure 6A:
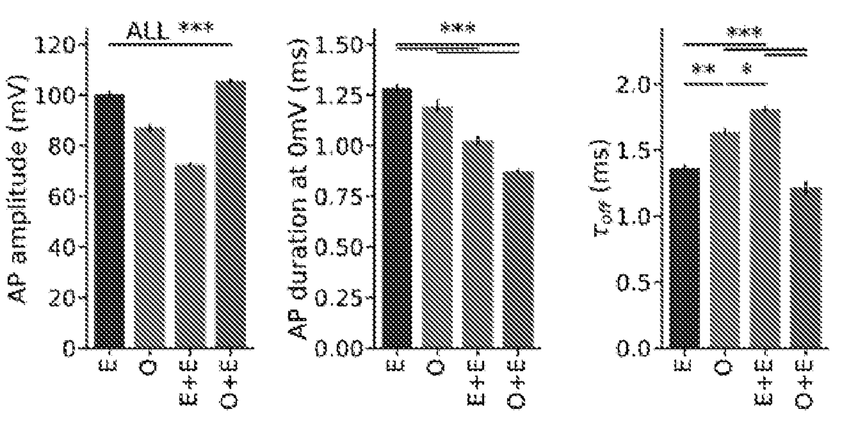
FIG. 6A shows a comparison of stimulus modes electrical-only (E), optical-only (O), optical and electrical co-stimulation (O+E) and all electrical co-stimulation (E+E, in which the optical stimulus period is replaced with an electrical ramp)

The characteristics of four stimulus modes are compared in FIG. 6A. The four modes are O, E, O+E and E+E (wherein the optical stimulus period is replaced with an electrical ramp). FIG. 6A shows key characteristics of each of these stimulus modes, including amplitude and duration of the AP and the time off constant $\tau_{off}$ given as the time for APs to decay to 36.8% of the peak amplitude value. For optical, n=21 cells, for electrical n=11 cells, for all-electrical n=7 cells, and for co-stimulation n=7 cells.

Mean amplitude for APs was significantly different for all stimulation methods (one-way ANOVA, $p<0.01$), with co-stimulation spikes having the largest amplitude (105.6±0.6 mV, n=7 cells) followed by electrical (100.2±1.4 mV, n=11 cells) and then optical (87.1±1.5 mV, n=21 cells). The mean spike duration at 0 mV was also significantly different (one-way ANOVA, $p<0.01$). Co-stimulation APs (0.87±0.01 ms, n=7 cells) had significantly shorter duration than electrically evoked APs (1.29±0.02 ms, n=11 cells, TukeyHSD p=0.001) and optically evoked APs (1.19±0.04 ms, n=21 cells, TukeyHSD, p=0.001).

The "off" time constant $T_{off}$, was not significantly different for co-stimulation and electrically evoked APs (co-stimulation 1.22±0.06 ms, electrical 1.36±0.03 ms, TukeyHSD, p=0.16) while optically evoked APs had significantly slower dynamics (1.63±0.03 ms, TukeyHSD, p=0.001). The similar co-stimulation and electrical-only off time constants suggest that the co-stimulation APs are predominantly driven by the electrical trigger pulse.

Figure 6B:
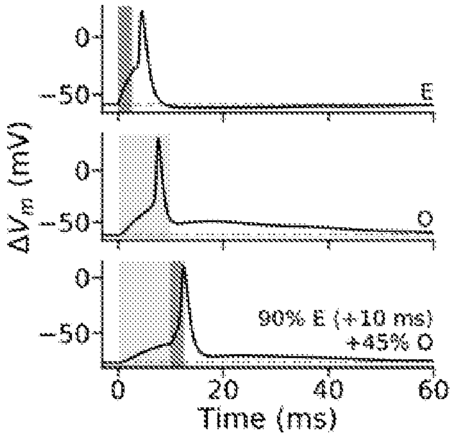
FIG. 6B shows a comparison of action potentials generated in response to electrical (E), optical (O) and optical and electrical co-stimulation (O+E)

FIG. 6B compared action potentials of electrical (E), optical (O) and optical+electrical (O+E) APs. The lighter shaded area indicates optical stimulus, while the darker shaded area indicates electrical stimulus. As can be seen, for O and O+E APs, the membrane remains slightly depolarised for tens of milliseconds after the cessation of optical stimulus and a slow repolarisation of approximately 40 ms is evident following the AP. This dynamic behaviour corresponds to the typical repolarisation following a subthreshold optical response.

Figure 6C:
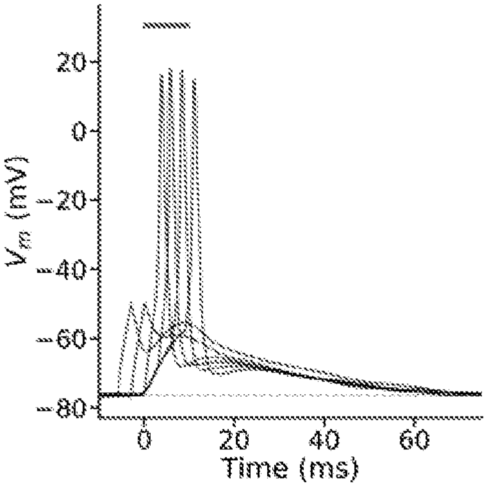
FIG. 6C shows a series of overlaid action potential traces generated by optical and electrical co-stimulation with varied delay time between the onset of the optical and electrical stimulus.
Figure 6D:
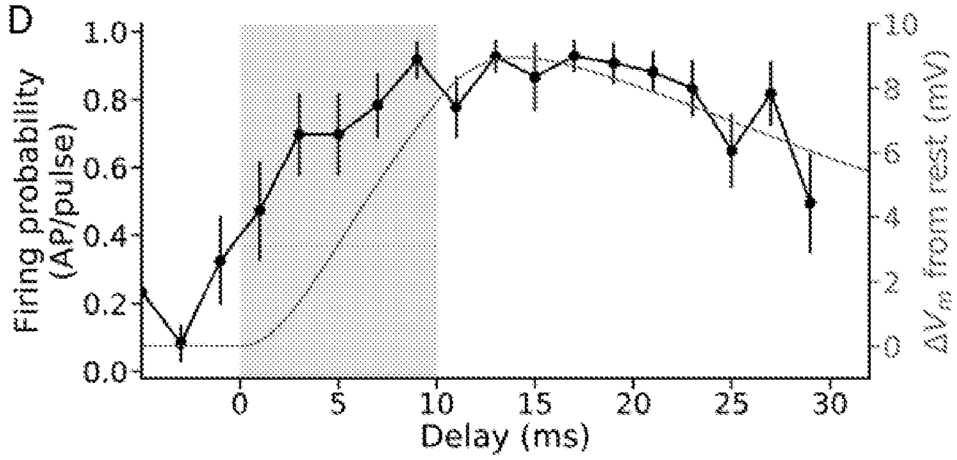
FIG. 6D shows the probability of optical and electrical co-stimulation to elicit action potentials based on the delay time between the optical stimulus and the electrical stimulus, overlaid with the average change in membrane potential.

To determine optimal timing of stimuli required to evoke a co-stimulation AP, the onset of the electrical stimulus was varied relative to the optical stimulus. Initially the onset of electrical stimulus preceded optical onset by 3 ms. The electrical stimulus was then moved by 2 ms in each subsequent presentation until it was lagging the start of optical stimulus by up to 30 ms. A series of delayed stimuli are shown overlaid in FIG. 6C, to demonstrate the temporal dependency of the co-stimulation effect. The optical pulse is indicated by the bar above the AP traces. APs are more likely to be fired when the electrical stimulus occurs after the onset of optical stimulus.

FIG. 6D shows the probability of co-stimulation stimuli to elicit APs based on the delay of the electrical pulse relative to the optical pulse. All the power levels considered here exceed the co-stimulation threshold across all delays where the electrical stimuli lag the onset of optical stimuli. The duration of the optical stimulus is indicated by the shaded region. For stimulus levels which are shown to produce co-stimulation APs, a threshold firing probability of 0.5 spikes per pulse is achieved when electrical stimuli are presented 3 ms after the onset of optical stimulation. The firing probability approaches one when electrical stimulus onset lags the onset of optical by 10 ms, which is also the point at which optical stimulus ceases but is before the maximum voltage change. In this example, it was observed that the firing probability remains relatively high for a period of time, e.g., of about 15 ms, after the cessation of optical stimulus, before decaying slowly. The average change in membrane potential resulting from subthreshold optical stimulation is shown overlaid in grey, and has a strong positive correlation with the firing probability (Pearson correlation coefficient $\rho=0.85$, $p<0.001$). The rate of change of membrane potential is poorly correlated with firing probability over the entire range of delays (Pearson correlation coefficient $\rho=0.11$, $\rho=0.66$), however during the period of optical stimulus the instantaneous rate of change of membrane potential is strongly positively correlated with firing probability (Pearson correlation coefficient $\rho=0.94$, $p<0.01$). This indicates that the probability of firing is related to both the optically-mediated membrane depolarisation and its rate of change. Multiple linear regression using $V_m$ and $$\frac{dV_m}{dt}$$

as the dependent variables yielded a strong correlation across the entire range of delays (Pearson correlation coefficient $\rho=0.91$, $p<0.01$;

$$P(\text{firing}) = 536 + 6.9V_m + 962\frac{dV_m}{dt}\Big).$$

Figure 6E:
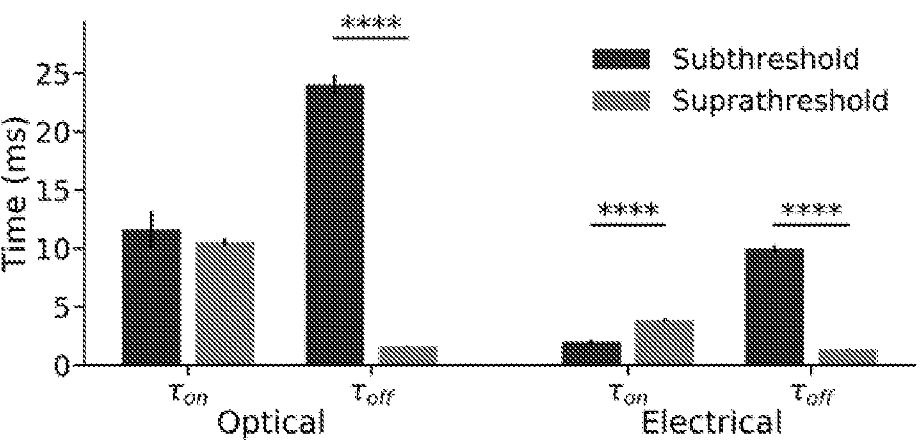
FIG. 6E compares time constants for subthreshold and suprathreshold optical and electrical stimulation.

The time constants for subthreshold optical and electrical stimulation can be seen in FIG. 6E, compared against suprathreshold stimulation. As expected, cells respond significantly differently to subthreshold stimulation compared to suprathreshold stimulation. Onset dynamics are in a similar order of magnitude for subthreshold and suprathreshold responses, but repolarisation is significantly faster following APs compared to subthreshold depolarisation. For optical stimuli the on AP dynamics were not significantly different between subthreshold and suprathreshold responses ($\tau_{on}$=11.7±1.6 ms for subthreshold, $\tau_{on}$=10.6±0.4 ms for suprathreshold, two tailed t-test, ρ=0.44). These relatively lengthy time constants are likely related to the slow depolarisation elicited by the 10 ms optical pulse. The off dynamics are significantly faster where an AP occurs ($\tau_{off}$=24.0±0.8 ms for subthreshold, $\tau_{off}$=1.63±0.03 ms for suprathreshold, $p<0.001$).

For electrical stimulation the $\tau_{on}$ was significantly shorter for subthreshold responses (2.0±0.2 ms) compared to suprathreshold responses (3.9±0.1 ms, two-tailed t-test, $p<0.001$). This surprising result is most likely related to the selected pulse parameters ensuring voltage threshold was only reached near the end of the 3 ms electrical pulse. The repolarisation of the cell was significantly faster for suprathreshold (1.36±0.03 ms) compared to subthreshold (1.0±0.3 ms, two-tailed t-test, $p<0.001$).

The strong correlation between optical depolarisation and firing probability and the similarity in characteristics between E and O+E APs suggests that during optogenetic co-stimulation voltage-sensitive ion channels and the opsins combine in an "additive" fashion to evoke co-stimulation APs. To examine whether this same relationship would exist simply through membrane depolarisation, a combination of two separate electrical stimuli was presented (denoted as 'all-electrical' co-stimulation, or E+E). In this test, the 10 ms optical pulse was substituted by a 20 ms electrical ramp with an amplitude and time course approximating that of the average membrane change from subthreshold optical stimulation.

Figure 7A:
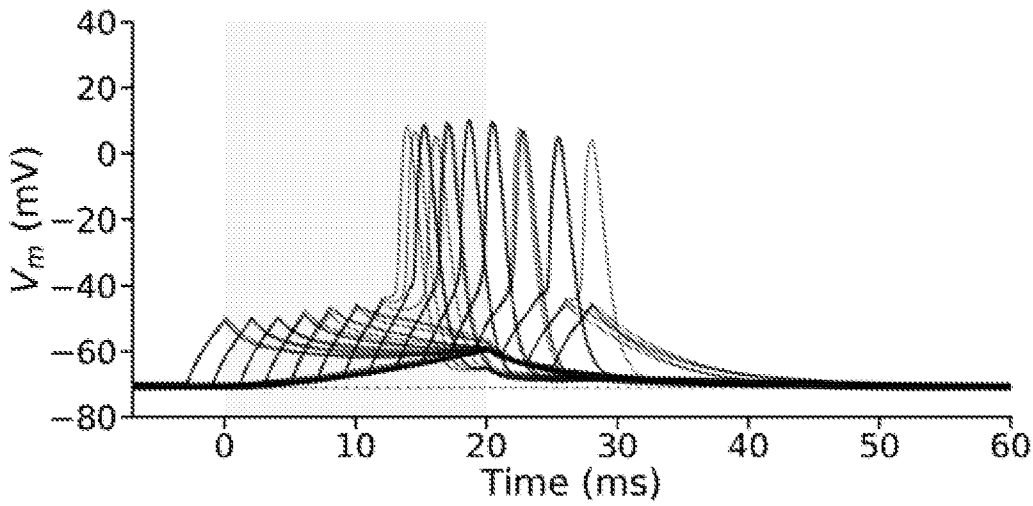
FIG. 7A shows a series of overlaid action potential traces generated by all-electrical (E+E) stimulation with varied delay time between the electrical ramp and electrical trigger pulse.

Voltage traces showing a typical cell response from all-electrical (E+E) stimulation with increasing temporal delay between the 3 ms electrical trigger pulse and the electrical ramp is shown in FIG. 7A. The shaded region indicates the duration of the electrical ramp. Several characteristics are shared with the co-stimulation APs in FIG. 6C, including the presence of two peaks (one for the ramp and one for the 3 ms trigger pulse), as well as evoked APs once the cell membrane was sufficiently depolarised. As with O+E stimulation, APs are more likely later in the electrical ramp.

Figure 7B:
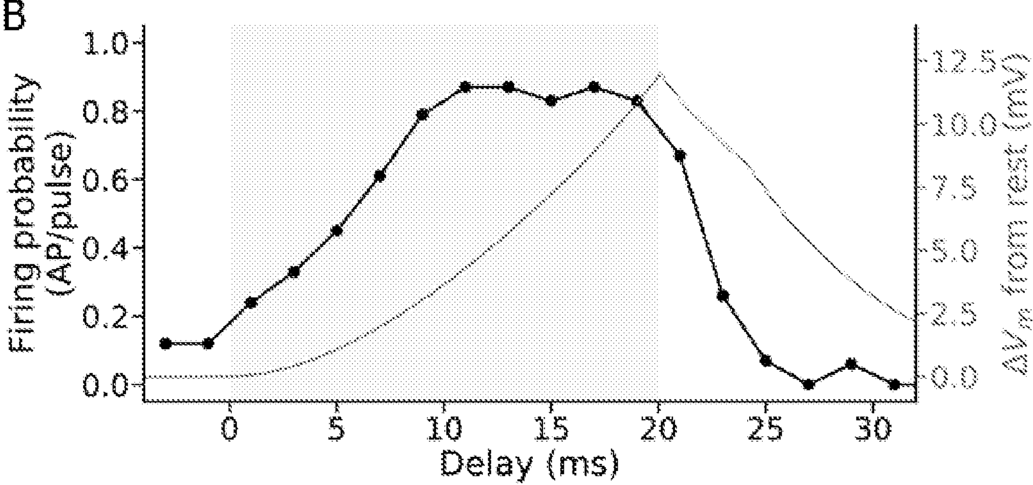
FIG. 7B shows firing probability as a function of delay time for all-electrical (E+E) stimulation, overlaid with the average change in membrane potential.

FIG. 7B shows the firing probability (APs per stimulus pulse) as a function of temporal delay for the all-electrical co-stimulation imitation. This is overlaid with the membrane potential change due to the 20 ms electrical ramp. The duration of the electrical ramp is indicated by the shaded region. Like optical stimulation, the peak firing probability is achieved after 10 ms and remains high throughout the duration of the ramp. Unlike optical stimulation, upon cessation of the electrical ramp stimulus the firing probability rapidly drops in a manner inconsistent with the relatively slow $\tau_{off}$=10.0±0.3 ms for subthreshold electrical stimulation. The firing probability for all-electrical co-stimulation has a weak positive correlation with the membrane voltage (Pearson correlation coefficient ρ=0.44, ρ=0.051), however the correlation with the instantaneous first derivative of the membrane potential yields a more positive result during the ramp (ρ=0.55, ρ=0.01). The correlation is stronger if only the period during the stimulus is considered, corresponding to $dV_m/dt>0$ (ρ=0.66, ρ=0.02).

Figure 7C:
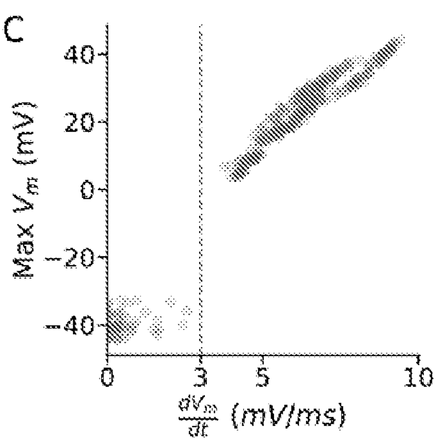
FIG. 7C shows the rate of membrane depolarisation plotted against the maximum membrane potential.

Co-Stimulation APs have Reduced $Na^+$ Inactivation Compared to Electrical-Only APs The firing probability of many cells is known to depend on the rate of change of membrane potential immediately preceding the stimulus. Referring to FIG. 7C, for the SGNs investigated in this example, the effect of rate of change of membrane depolarisation on AP generation was investigated through application of varying gradient current ramps (n=6 cells). Initially the ramp was tuned until APs were generated, however as the gradient of the ramp was subsequently reduced (with the same peak current), APs were eventually abolished. This effect is usually attributed to the effect of increased $Na^+$ inactivation during slower depolarisations.

Figure 7D:
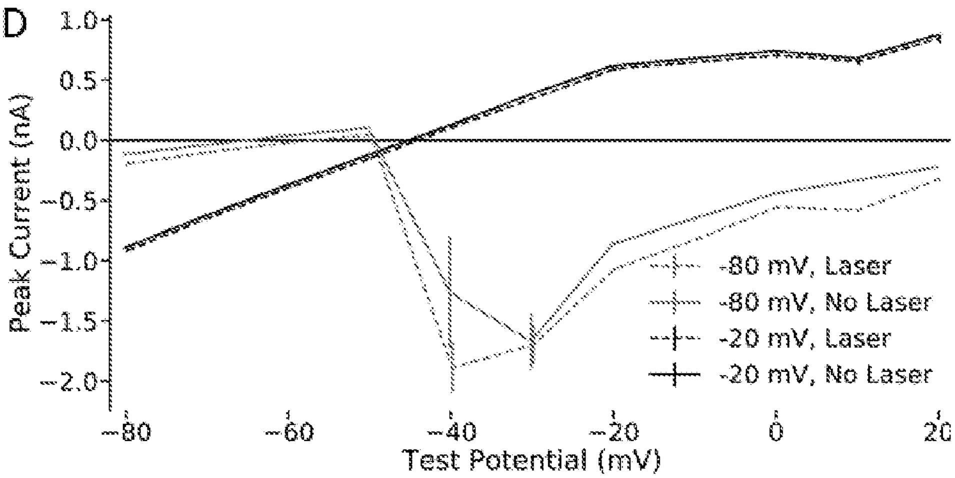
FIG. 7D shows the relationship between maximum evoked current and test potential for an electrical conditioning pulse followed by an electrical test pulse, with and without an optical pulse prior to the electrical pulse.

As optical stimuli do not directly activate $Na^+$ ion channels, they may allow membrane depolarisation with reduced $Na^+$ inactivation. To test this, a 300 ms conditioning pulse (at either −20 mV or −80 mV) was followed by a 200 ms test pulse (ranging from −80 mV to +10 mV). The relationship between maximum evoked current and voltage was assessed, with and without a 50 ms optical pulse immediately prior to the test pulse. Referring to FIG. 7D, for −80 mV conditioning pulses, a transient inward current akin to $I_{Na}$ was evoked for test pulses above −50 mV. For a conditioning pulse of −20 mV the transient currents were initially inwards but became predominantly outward after a test pulse of −20 mV or above. The inclusion of optical stimuli during the conditioning pulse did not significantly alter the amplitude of the transient currents for either −80 or −20 mV conditioning pulses, suggesting that the optical pulse did not increase $Na^+$ inactivation (two sided Kolmogorov-Smirnov; at −80 mV, score=0.22, ρ=0.96, at −20 mV, score=0.11, ρ=1.0).

Figure 7E:
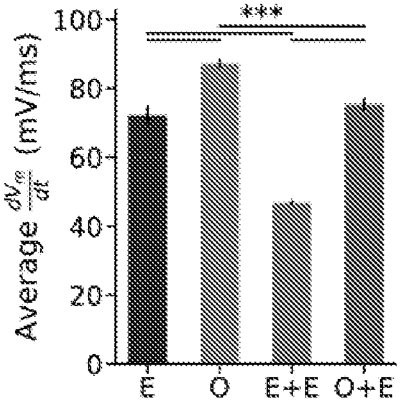
FIG. 7E shows the average $dV_m/dt$ during the upstroke of action potential spikes for various stimulation modes.

Another way to investigate the degree of $Na^+$ inactivation is to measure the average $dV_m/dt$ during the upstroke of spikes, measured from when $dV_m/dt$ exceeds the derivative threshold until the peak $V_m$. As shown in FIG. 7E, there was a significant difference between the average $dV_m/dt$ for O+E and E+E co-stimulation (O+E=75.3±1.8 mV/ms, E+E=46.9±0.8 mV/ms, two-tailed t-test $p<0.001$, FIG. 7E). This result is consistent with a higher inactivation of $Na^+$ channels during the electrical ramp compared to the optical depolarisation during O+E co-stimulation. The average derivative from O+E co-stimulation was not significantly different from electrical-only stimulation (two-tailed t-test, ρ=0.33) however was significantly lower than with optical-only stimulation (87.16±1.38 mV/ms, $p<0.001$) consistent with reduced reliance on $Na^+$ channels during optically-evoked APs. These results indicate that optogenetic co-stimulation may be used to increase cell excitability through membrane depolarisation for extended periods of time without excessive $Na^+$ inactivation.

Referring now to FIG. 8A to 8E, pulse trains were presented at 10, 20, 33 and 50 Hz, to examine the effectiveness of optogenetic co-stimulation to increase spike rate. A combination of subthreshold and suprathreshold optical and electrical stimuli were tested (varying between 0% and 140% of single pulse threshold power). For consistency, the same pulse lengths were used as with the single pulse protocols (10 ms optical and 3 ms electrical), and the electrical stimulus was fixed to lag 3 ms after the onset of optical stimulus (corresponding with the firing probability of 0.5 in FIG. 6D).

Figure 8A:
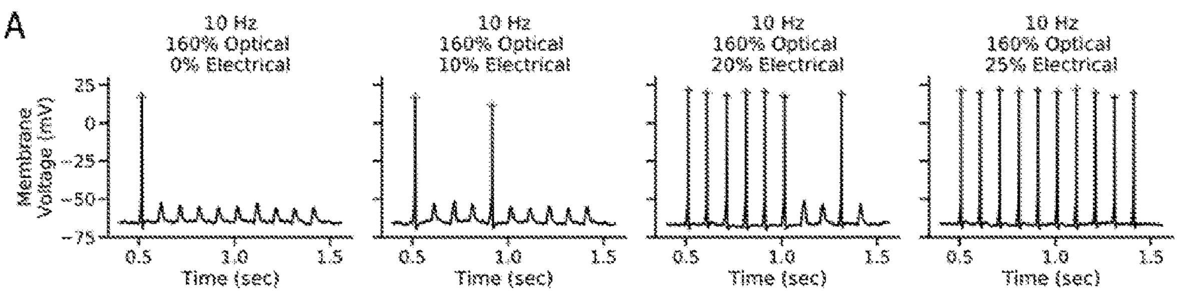
FIGS. 8A and 8B show voltage traces typical of cell responses to combined optical and electrical pulse trains at 10 Hz and 20 Hz, respectively.
Figure 8B:
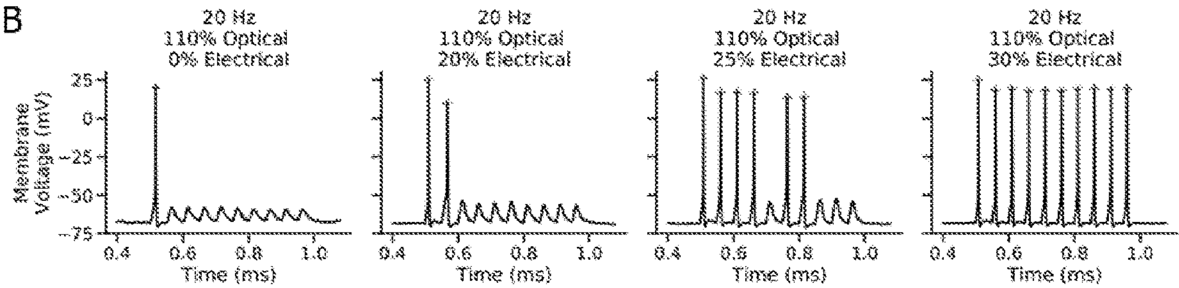
Figure 8C:
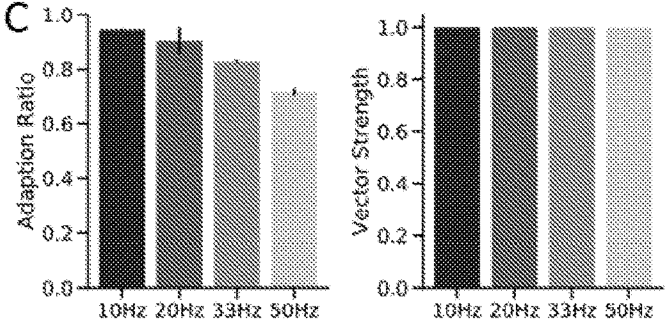
FIG. 8C shows adaption ratio and vector strength for pulse trains at various frequencies.

Typical cell responses to combined optical and electrical trains at 10 Hz and 20 Hz are shown in FIGS. 8A and 8B, respectively. In these examples, optical power was held constant while electrical power increased as shown in the panels from left to right. The number of APs fired increased as electrical power was increased. Co-stimulation responses were phase locked to the stimulus (vector strength near one for all experimental cases). As shown in FIG. 8C, there was evidence of adaption in subsequent pulses in the pulse trains. The adaption ratio (defined as the amplitude of the last spike in the train to the first) fell from near one at 10 Hz (0.94±0.00, n=10 cells), to 0.69±0.01 at 50 Hz (n=10 cells). Adaption was slightly higher but not significantly different (two-tailed t-test, ρ=0.49) at 50 Hz for co-stimulation (0.73±0.02, n=5 cells) compared to electrical-only stimulation (0.77±0.01, n=5 cells).

Figure 8D:
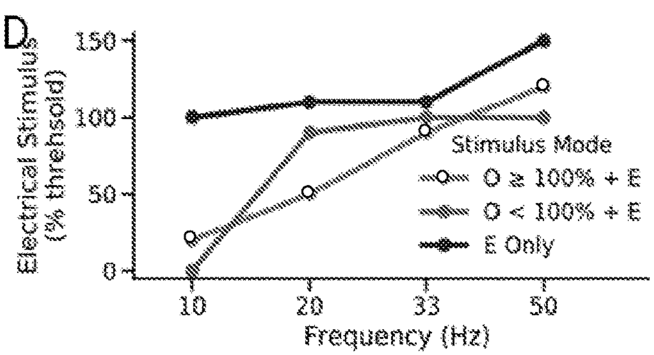
FIG. 8D shows a graph of the electrical stimulus power level required to achieve a firing rate of 0.5 for different stimulus modes and at various pulse frequencies.

The electrical stimulus level required to achieve a firing rate of 0.5 for different stimulus modes is shown in FIG. 8D. For a given optical stimulus level, the required electrical stimulus to evoke an AP increased with frequency. Surprisingly, the electrical stimulus for subthreshold and suprathreshold optical co-stimulation were similar, and in both cases were reduced compared to electrical-only stimulation (n=12 cells). This is likely related to the delay time of 3 ms, which is shorter than $\tau_{on}$ which is in the order of 10 ms (see FIG. 6E). At all frequencies, co-stimulation firing probabilities exceed electrical-only and optical-only firing probabilities.

Figure 8E:
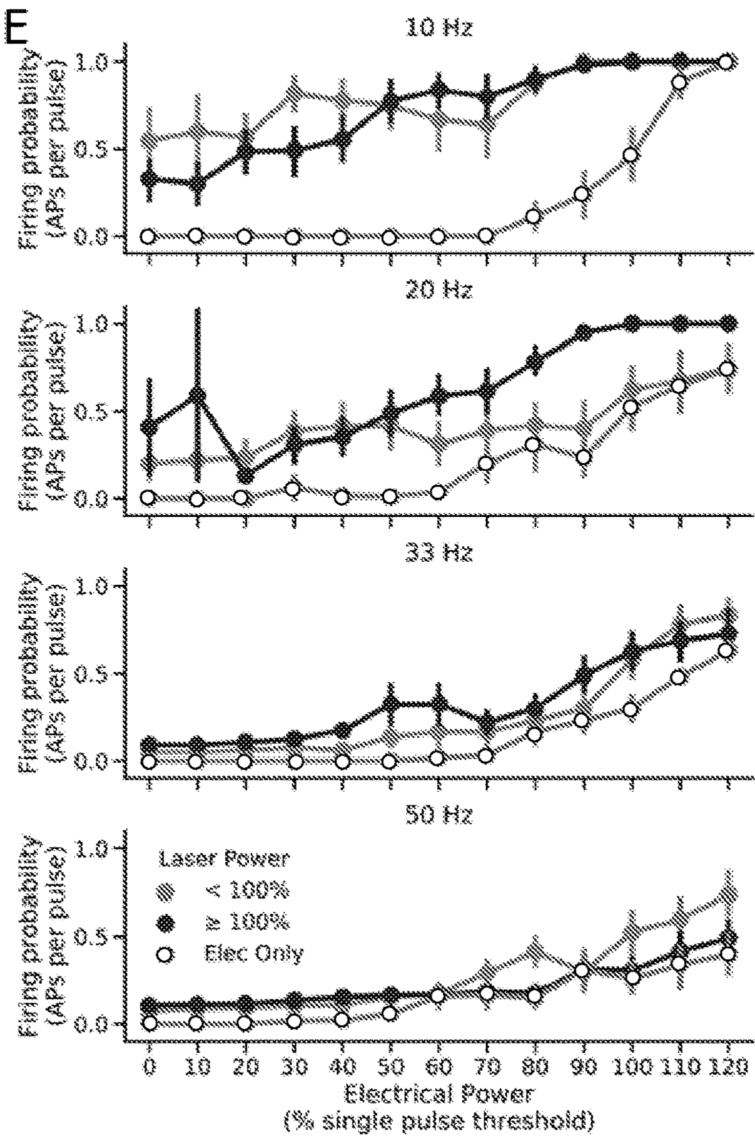
FIG. 8E shows a comparison of average firing probabilities for increasing electrical power, grouped by pulse frequency.

FIG. 8E compares average firing probabilities for increasing electrical power, grouped by pulse frequency (n=12 cells). Black dots indicate suprathreshold optical power, grey dots indicate subthreshold optical power and white dots indicate the absence of optical stimuli. The number of APs generated for a given optical power level increased with increasing electrical power. At all frequencies, co-stimulation (with either subthreshold and suprathreshold optical stimulus), lead to a higher probability of firing compared to electrical-only stimulation ($p<0.05$, Kolmogorov-Smirnov two sample test), while subthreshold and suprathreshold optical were not significantly different ($p>0.05$) although the firing probabilities of the modalities converged at frequencies close to the in vitro stimulation limit for this cell type.

For optical stimulation on its own, pulse trains at 10 Hz achieved a firing probability close to 0.5. With the co-stimulation technique, it was possible to drive pulse trains with 0.5 firing probability at up to 33 Hz, at least three times faster than using optical stimulation alone, while maintaining lower electrical currents compared to all electrical stimulation.

DISCUSSION

Optogenetic-based implants are a promising avenue for improving the performance of prosthetic devices. They are of interest to cochlear implants which are susceptible to crosstalk between channels due to the spread of electrical activation in the tissue. Optical stimulation has a larger power requirement than electrical stimulation, which limits its application in battery powered devices. In addition, most channelrhodopsin variants have slower temporal dynamics compared to the pulse rates typically used in devices, which can range from 250 to more than 4,000 pulses per second per electrode in cochlear implants. While significant work has been done in generating fast spiking channelrhodopsin mutants, other approaches that complement these faster opsins may be beneficial.

This example demonstrates that combining subthreshold optogenetic stimulation with subthreshold electrical stimulation can evoke co-stimulation APs in spiral ganglion neurons and increase pulse train firing probabilities compared to standalone optical stimulation. This approach can likely be used to enhance the performance and application of existing engineered opsins and optics-based probes without requiring significant reengineering of the opsin itself.

The ChR2/H134 opsin considered in the present example is a high photocurrent variant with slower kinetics compared to wild type ChR2. Optical-only stimulus evoked pulse trains in vitro have previously been driven at frequencies from 5 Hz or up to 100 Hz at a variety of power levels, while in vivo firing rates of up to 70 Hz have been reported. In general the firing probability of optically evoked APs is limited by the off time constant of the opsin, which is around 18 ms for ChR2/H134. With optical stimulation alone, a firing probability near 0.5 was found for 10 Hz pulse trains. Though this is on the lower side of ranges reported in previous results, it is likely constrained by the stimulus parameters selected; shorter, higher power pulses could potentially provide further benefits for optogenetic co-stimulation. Indeed, higher frequencies have previously been achieved with electrical-only stimulus evoked APs in vitro, with SGNs maintaining firing probabilities above 0.5 at up to 66 Hz using 0.3 ms, 1.5 nA pulses. Firing rates of up to 1 kHz have previously been reported in vivo, though these are not replicated in the in vitro preparation.

Relationship Between Co-Stimulation Firing Probability and $Na^+$ Inactivation

In the present example, the firing probability for co-stimulation stimuli was demonstrated to relate to both the change in membrane potential and the instantaneous rate of change of membrane potential during the optical stimuli. This dual dependency is consistent with previous in vivo observations of a dynamic voltage threshold. That is, the threshold voltage for AP generation increases as the rate of change of the membrane potential decreases, which in turn implies a positive correlation between firing probability and $dV_m/dt$. This response is a result of synchronised activation and inactivation of $Na^+$ channels. Typically $Na^+$ inactivation occurs more slowly than activation, however when depolarisation is sufficiently slow inactivation can occur within the same time scale. As a result of this synchronisation, following a slow depolarisation the pool of $Na^+$ channels available to generate an AP is lower compared to after a fast depolarisation and cell excitability is therefore reduced. It has also been well established that $Na^+$ inactivation can occur even when the channel has not first entered the open state. This closed-state inactivation occurs at moderately depolarised membrane potentials and along with open state inactivation may further contribute to reduced excitability following slow depolarisations.

Sodium channel dynamics during slow depolarisation are of interest for the O+E co-stimulation described in the present example due to the long subthreshold optical depolarisation. Interestingly, the long tail on the firing probability during O+E co-stimulation (FIG. 6D, with APs generated up to 30 ms after the onset of optical stimulus) appears to contradict the view of synchronised activation and inactivation. In contrast to the significantly lower $dV_m/dt$ evident with E+E co-stimulation compared to electrical-only (FIG. 7E) the membrane potential derivative during O+E APs remained high, suggesting that $Na^+$ inactivation did not increase significantly during long periods of optical depolarisation. This surprising result can be explained by separate open state and closed state inactivation processes. During E+E co-stimulation $Na^+$ channels are used to depolarise the cell (resulting in open-state inactivation) and, as the depolarisation is slow, a significant number of ion channels enter this state. For O+E co-stimulation the depolarisation is largely through the channelrhodopsin ion channel, which reduces the amount of open-state inactivation that occurs, leaving the cell in a more excitable state.

Comparison to Infrared Neural Stimulation

Electrical stimulation has previously been applied in combination with infrared neural stimulation (INS) with 1875 nm light in a study using 2 ms optical and electrical stimuli, with 0-2.5 ms delay between the optical and electrical pulses. INS is known to be a thermally driven process, mostly dependent on the rate of change of temperature in the tissues. Previous modelling has shown a logarithmic relationship between radiant intensity and temperature increase in the tissues, which supports the logarithmic relationship between the required optical and electrical energy for INS co-stimulation. A consequence of this logarithmic response is that, as the optical power in INS drops below 70%, an exponentially increasing electrical power is required to reach co-stimulation threshold.

INS modulates neuronal activity using rapid changes in temperature, In contrast, optogenetic stimulation is driven by direct changes in ionic conductance as the opsins absorb photons. This is a distinctly different mechanism to INS. The optogenetic co-stimulation approach may help to preserve the spatial advantages of optogenetics, while alleviating some of the practical issues of optical-only based implantable devices including high-power consumption and fast control of neurons.

The ability to evoke APs with relatively low optical and electrical power suggests a higher sensitivity to optical stimulus level using optogenetic co-stimulation, and hence this technique is likely to be more energy efficient compared to infrared co-stimulation. The effect of the optical stimulus in both cases was to create periods of enhanced excitability. As INS is a thermally mediated process, the duration of the excitable period could be controlled by increasing the optical power level to generate a larger temperature increase. However, it is recognised that excess heat can lead to cell damage or INS mediated inhibition. For optogenetic co-stimulation the shape of the depolarisation results from radiant intensity and the duration of the pulse. This example utilises longer pulses with increased delays compared to previous INS studies. Additionally, due to the channel kinetics of opsins, the peak current can often occur after the light source is turned off, while slower closing dynamics of the ion channels means that the enhanced excitability can persist for significant periods after the cessation of stimulus. Additionally, shorter and higher power light pulses could reduce the time taken for the cell to reach peak excitability down from the 10 ms period reported here. The ability to control the degree and onset of enhanced excitability may provide additional tools for adaptive control schemes in implantable devices.

Optical Irradiance and Power Consumption

Typical energy requirements for achieving APs in the cochlea using optogenetic stimulation alone (2 μJ/mm$^2$) have previously been shown to be ten times higher than for electrical stimulation (0.2 μJ/mm$^2$). Additionally, many optical devices with external light sources have optical efficiency in the order of 10-30%, suggesting that optical neural interfaces may require several orders of magnitude more power than electrical devices. Shifting the burden of activation from optical to electrical excitation as in the method of the current disclosure may reduce the power required to evoke APs. It will be appreciated that the exact power saving would depend on the pulse parameters selected and the characteristics of the stimulating interface.

In addition to reducing power requirements, the co-stimulation technique of the presently disclosed method may also reduce the blue light exposure of tissues. Blue light toxicity in light stimulation is an emerging concern; while several studies have shown viral delivery of optogenetic ion channels to be safe over months, other studies have shown a link between blue light exposure and neuronal death in vitro in the retina. It is known that, in the retina, excess blue light can modify all-trans retinal (ATR) (which is naturally expressed in mammals and a key part of the operating mechanism of channelrhodopsin) and cause a subsequent interruption to cellular signalling. Increased blue light toxicity is associated with higher power levels, and so reducing the radiant exposure, or allowing faster control of red-shifted opsins may reduce the potential for damage.

Recent research efforts into engineered opsins such as "f-Chrimson" or "Chronos" have focused on decreasing $\tau_{on}$ and $\tau_{off}$ to allow neurons to be optically driven at higher spike frequency. As the optogenetic co-stimulation approach is unlikely to be linked to specific opsins, the ability to drive faster spikes with optogenetic co-stimulation may allow researchers to focus on biocompatibility above pure opening and closing dynamics when designing future opsin variants.

Example 2

Figure 9:
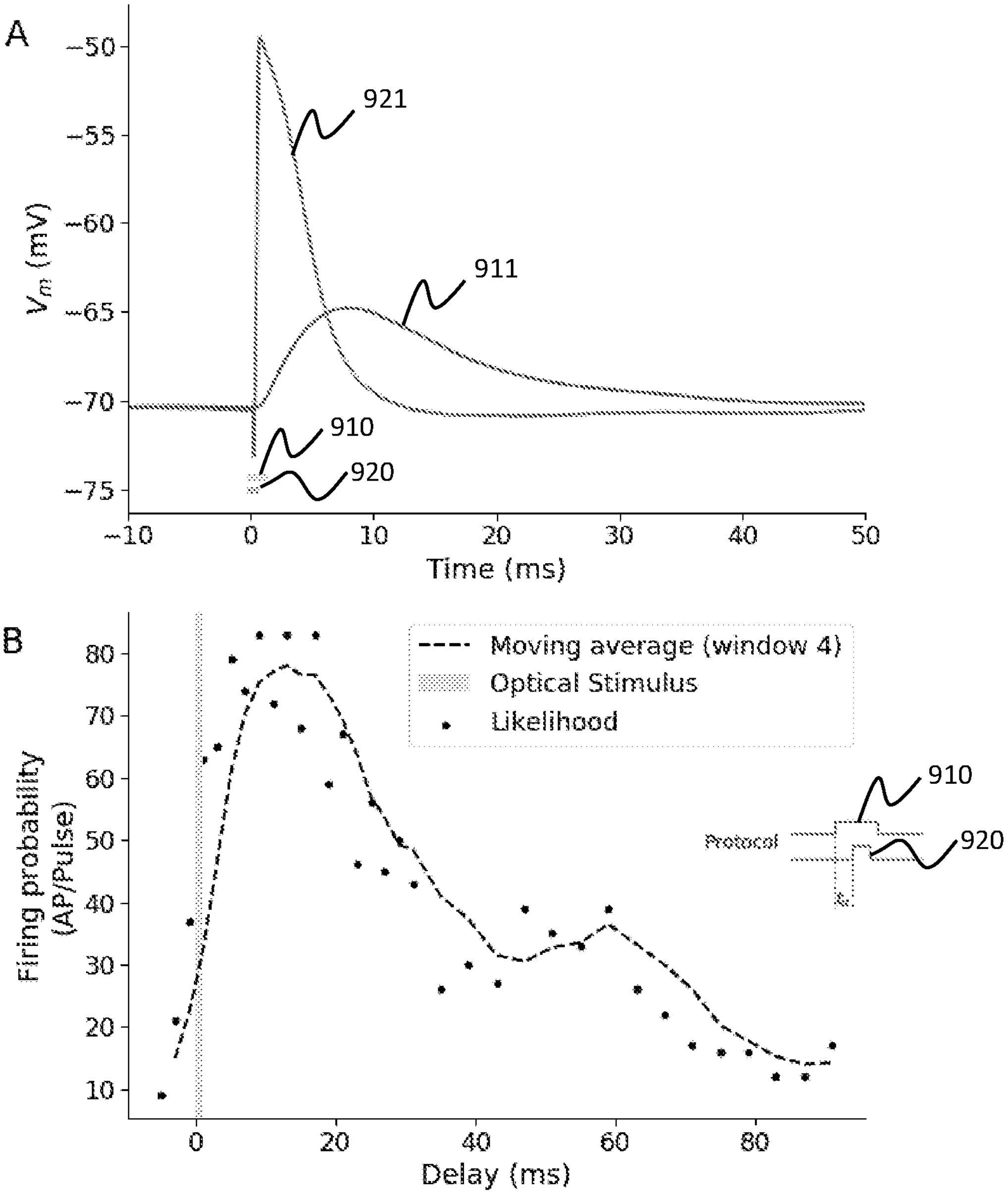
FIG. 9 shows a response of single cell membranes in-vitro to individually applied subthreshold optical and subthreshold electrical pulses (panel A) and the firing probability of the membranes when the subthreshold optical and subthreshold electrical pulses were applied as a hybrid stimulation (panel B)

Electrophysiology recordings were performed on cultured spiral ganglion neurons from ChR2-H134R transgenic mice to examine spike shape and the post-stimulus facilitation period in single cells. Referring to FIG. 9, the cells were subjected to 1 ms optical pulses 910 and 300 μs monophasic electrical pulses 920. Threshold stimulus was defined as the power level where action potentials were evoked for at least half of the presented stimuli. As shown in FIG. 9, panel A, for individually presented single pulses, there was a dramatic difference in the response of the cell membrane to subthreshold stimuli. On average, the response 921 of the membrane to subthreshold electrical stimuli was a sharp increases in membrane potential followed by a rapid decay immediately after the cessation of electrical stimulus. In contrast, the response 911 of the membrane subthreshold optical stimuli was a slow rise in membrane potential which continued after the cessation of optical stimulus followed by a decay in membrane potential over 30-50 ms.

Referring to FIG. 9, panel B, hybrid stimuli were then presented (electrical at 30-80% of threshold and optical at 80-100% of single pulse threshold) with a variable delay. When the electrical pulse preceded the optical pulse ($t_d$<0), firing probability increased from less than 10% to almost 40%. The increase of firing probability by almost 40% was observed when the electrical pulse was presented 1 ms before the optical pulse ($t_d$=−1 ms). When the electrical pulse lagged the optical pulse ($t_d$>0), firing probability increased to a maximum (83%) when the electrical pulse was applied 9 to 13 ms after the start of the optical stimulus. Firing probability fell below 50% when the electrical pulse was applied more than 30 ms after the start of the optical stimulus. However, action potential facilitation (defined in this example as 30-40% firing probability) persisted for up to 60 ms after the start of the optical stimulus.

Example 3

Figure 10A:
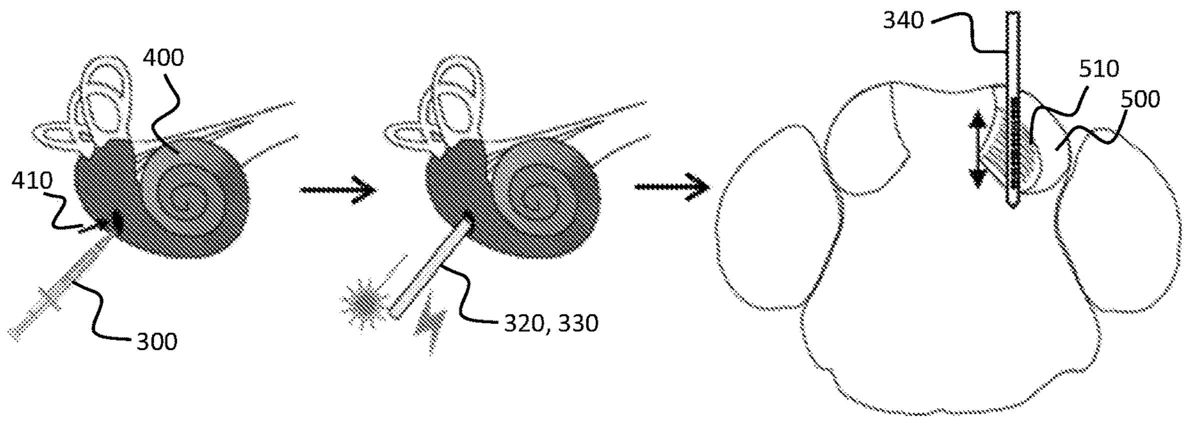
FIG. 10A illustrates an in-vivo experimental protocol used in transgenic mice.

Referring to FIG. 10A, transgenic mice expressing ChR2-H134R in spiral ganglion neurons (SGNs) via the parvalbumin promoter were acutely deafened by infusion of 10% neomycin solution 300 through the cochlear round window to eliminate the possibility of hair cell-mediated auditory responses. An optical fibre with an attached platinum wire 320, 330 was inserted 1-2 mm into the round window 410 of the cochlea 400. Optical, electrical or hybrid stimulation was delivered using the optical fibre 320 and platinum wire 330. During stimulation, neural recordings were made from the inferior colliculus 510 of the auditory midbrain 500 using a 32 channel recording array 340.

Expression of ChR2-H134R was confirmed histologically via a ChR2 antibody to mirror the localisation of EYFP (enhanced yellow fluorescent protein) in spiral ganglion neuron cell bodies, peripheral fibres and central fibres. The strongest fluorescence was localised to the membrane of spiral ganglion neurons. Additionally, ChR2-H134R was present in inner hair cells and more weakly in the outer hair cells of adult transgenic mice. This expression pattern was evident throughout the cochlea, from the basal turn to the apical turn.

The mice were acutely deafened with neomycin to reduce the possibility of hair cell-mediated auditory responses. Following acute exposure to neomycin, there was mid-high frequency hearing loss with significantly elevated tone-pip thresholds for 8, 16 kHz and 32 kHz compared to pre-deafening thresholds ($p<0.05$ two-way RM ANOVA). The efficacy of the acute neomycin deafening procedure was verified histologically in a subset of mice which showed complete or near complete loss of inner and outer hair cells (n=2).

Figure 10B:
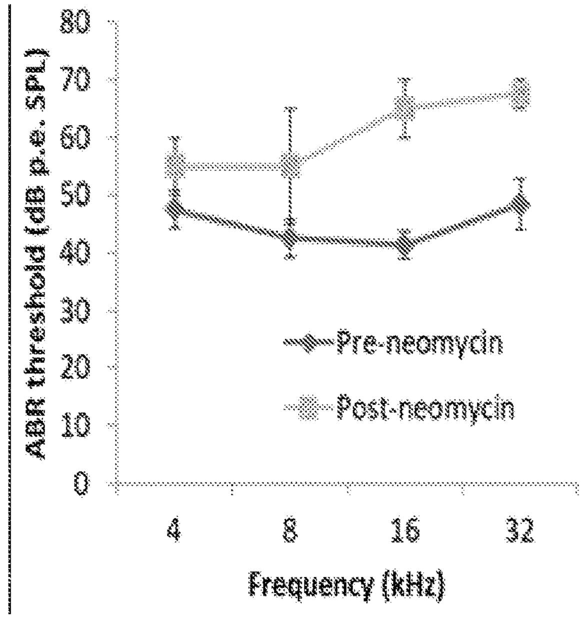
FIG. 10B shows a comparison of transgenic mouse tone pip ABR thresholds before and immediately after neomycin exposure.

FIG. 10B shows transgenic mouse tone pip ABR thresholds before and immediately after neomycin exposure. Acute exposure to neomycin resulted in mid-high frequency hearing loss with significantly increased tone-pip thresholds for 8, 16 kHz and 32 kHz compared to pre-deafening thresholds ($p<0.05$ two-way RM ANOVA). The effectiveness of the acute neomycin deafening procedure was verified histologically in a subset of mice which showed complete or near complete loss of inner and outer hair cells (n=2).

Thresholds

Threshold power levels were defined for optical and electrical pulses, respectively, as the lowest stimulus power level required to elicit a normalised spike rate of at least 0.3 (that is a 30% increase between spontaneous and maximum firing rates).

Hybrid electrical (250 μs) and optical (1 ms) pulses were then presented at varying levels above and below threshold (with the electrical pulse delayed with respect to the optical pulse). The start of the electrical pulse was delayed by a delay $t_d$ with respect to the start of the optical pulse, so that when $t_d$=750 μs both the optical and electrical pulses end simultaneously. The delays tested were 0 μs (i.e. no delay), 750 μs, 1750 μs, 2750 μs and 3750 μs.

Figure 11:
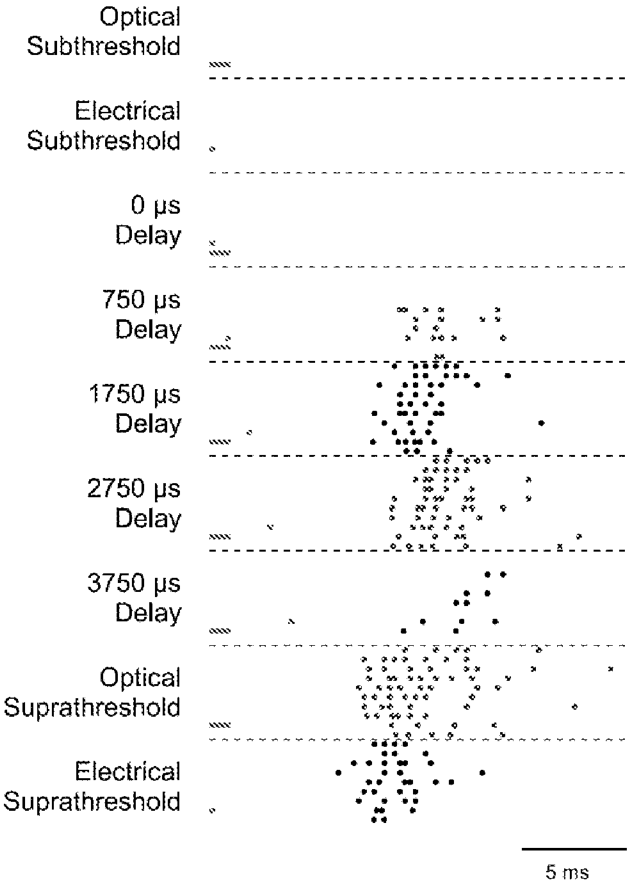
FIG. 11 shows a raster plot indicating when a neural response was detected after sub-threshold optical, sub-threshold-electrical and combined optical and electrical (hybrid) stimulation at various time delays.
Figure 12:
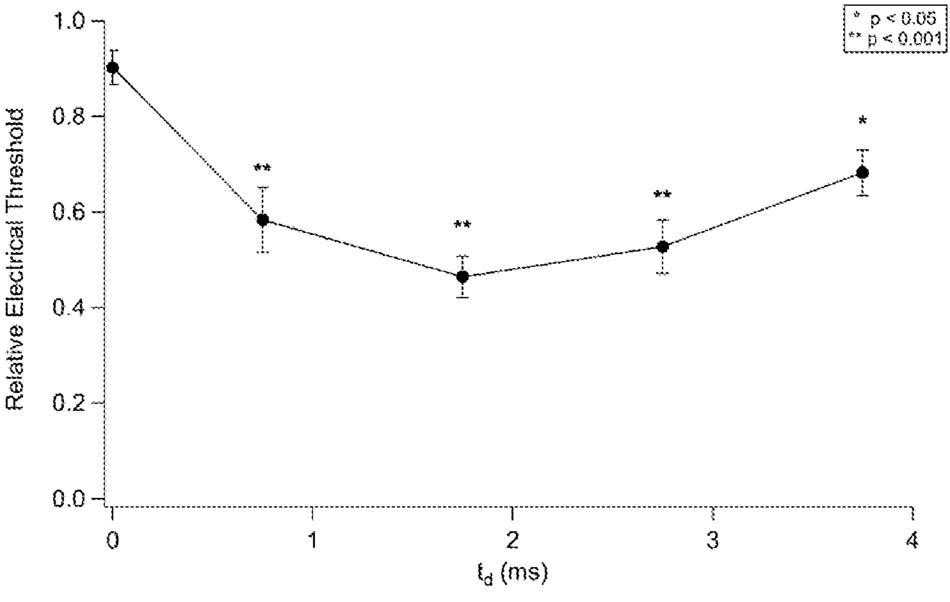
FIG. 12 shows the percentage of the electrical stimulation threshold at which a neural response was elicited for hybrid stimulation of 9 cochleae at various delays between the start of the optical pulse and the start of the electrical pulse.

FIG. 11 is a raster plot indicating when a neural response was detected. The pulse timing is illustrated in grey on the left hand side of the plot by the bar (optical stimulus) and square dot (electrical stimulus). It can be seen that sub-threshold optical and sub-threshold electrical stimuli applied individually did not evoke neural responses. By contrast, the application of these stimuli in combination elicited activity in the inferior colliculus. In this example, neural responses were observable where the hybrid pulses were presented with a delay between the start of the optical pulse and the start of the electrical pulse. In this example, the electrical stimulus was 64% of threshold and the optical stimulus was 70% of threshold FIG. 12 shows the percentage of the electrical stimulation threshold at which a neural response was elicited for hybrid stimulation of 9 cochleae at various delays between the start of the optical pulse and the start of the electrical pulse. In this example, when the start of the electrical pulse coincided with the start of the optical pulse (no delay), there was a minimal effect on electrical threshold. When the start of the electrical pulse was delayed after the start of the optical pulse, neural responses were detected with subthreshold levels of both optical power and electrical power. This effect was observed with delays of up to 3.75 ms, where the start of the electrical pulse occurs after cessation of the optical pulse.

Entrainment Rates

The response in the inferior colliculus to bursts of hybrid stimuli or optical stimuli presented at the cochlea was assessed to evaluate the temporal performance of hybrid stimulation compared to optical stimulation alone. The bursts of stimuli were each 300 ms in duration and presented at various pulse rates.

Figure 13:
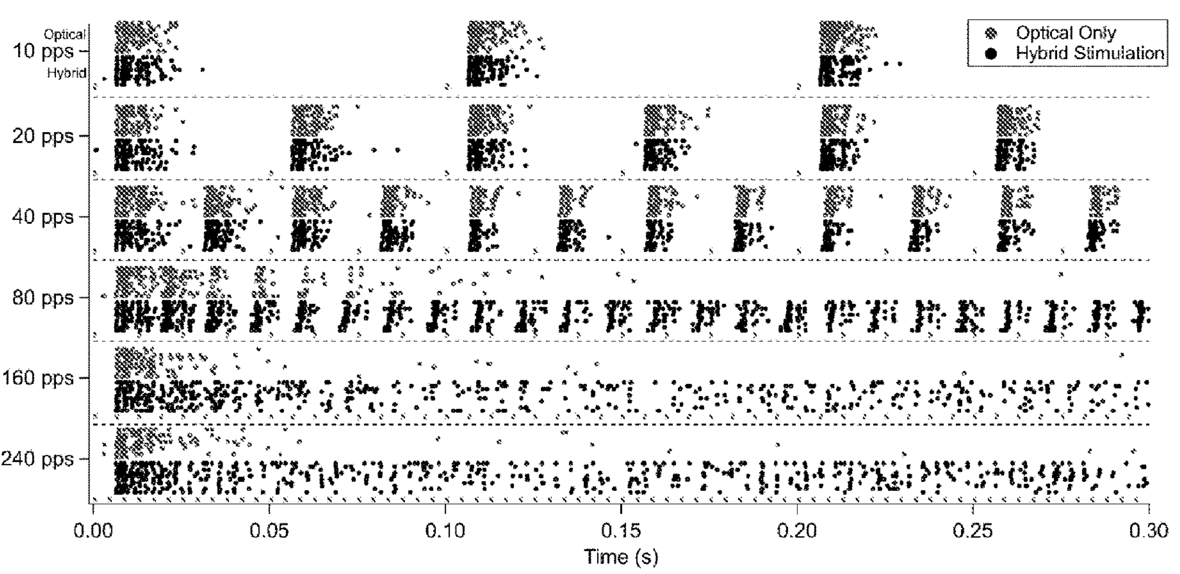
FIG. 13 shows a raster plot comparing entrainment achieved by optical only and hybrid stimulation for different stimulation rates.

FIG. 13 shows a raster plot comparing entrainment achieved by optical only and hybrid stimulation. At 40 pps, both stimuli have robust entrainment, but at 80 pps only the hybrid stimuli showed entrainment. At the maximum rate tested (240 pps), there are very few responses recorded after the initial onset of the optical-only stimuli. By contrast, at 240 pps the hybrid stimulation was able to evoke responses over the whole 300 ms stimulation period.

Figure 14:
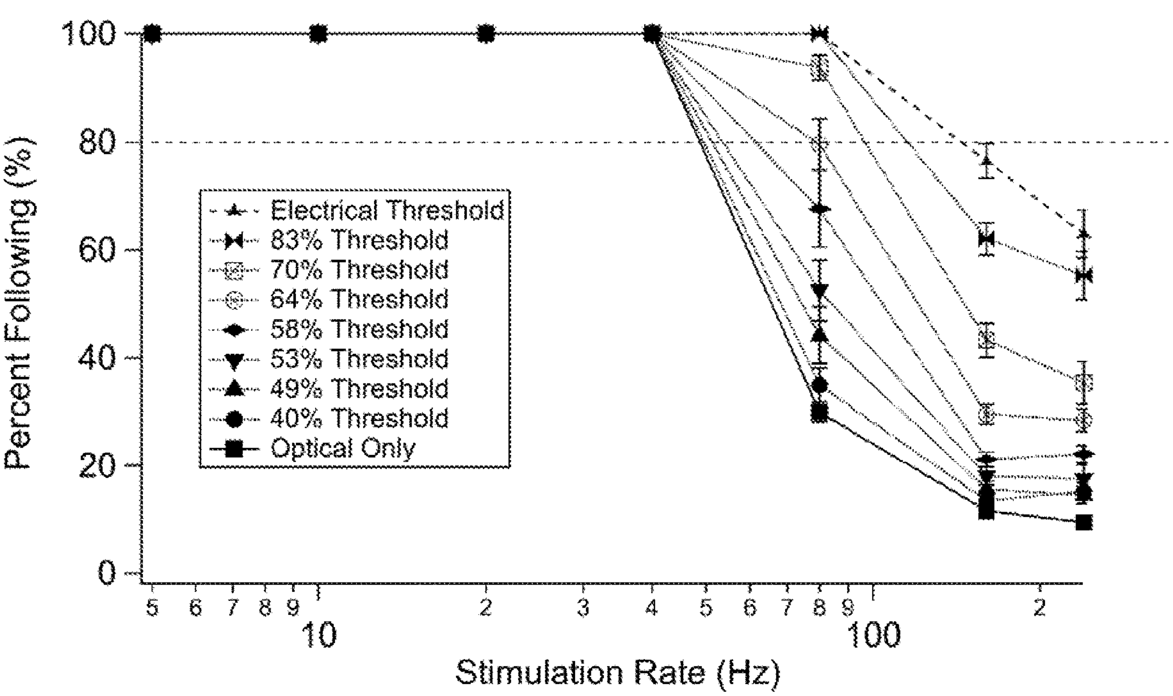
FIG. 14 shows an example of the percent following for suprathreshold optical stimulation alone and hybrid stimulation.

To better quantify the stimulation, the maximum following rate (MFR) was found (i.e. where 80% of triggers had at least one spike in response (80% "percent following")). To avoid overlapping windows at high pulse rates, a fixed 6-10 ms post stimuli window was used to count spikes. FIG. 14 shows an example of the percent following for suprathreshold optical stimulation alone and hybrid stimulation (suprathreshold optical with increasing levels of electrical from 40% of threshold to threshold). In this example, as the electrical current was increased, the percent following increased and the maximum following rate shifted from 51 Hz to 122 Hz.

Figure 15:
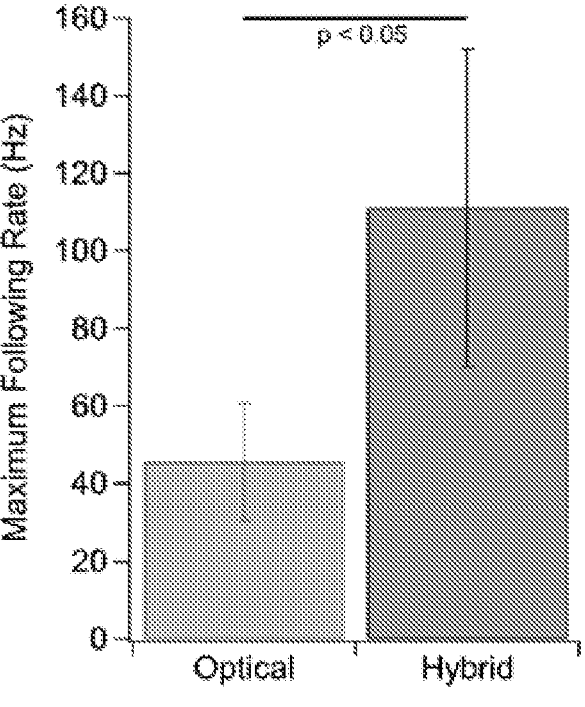
FIG. 15 shows the average increase in following rates when using hybrid stimulation compared to using optical stimulation alone.

FIG. 15 shows the average increase in following rates when using hybrid stimulation compared to using optical stimulation alone (n=4). With hybrid stimulation a maximum following rate of 111 Hz was achieved, compared to just 46 Hz for optical alone.

Spread of Activation

Figure 16:
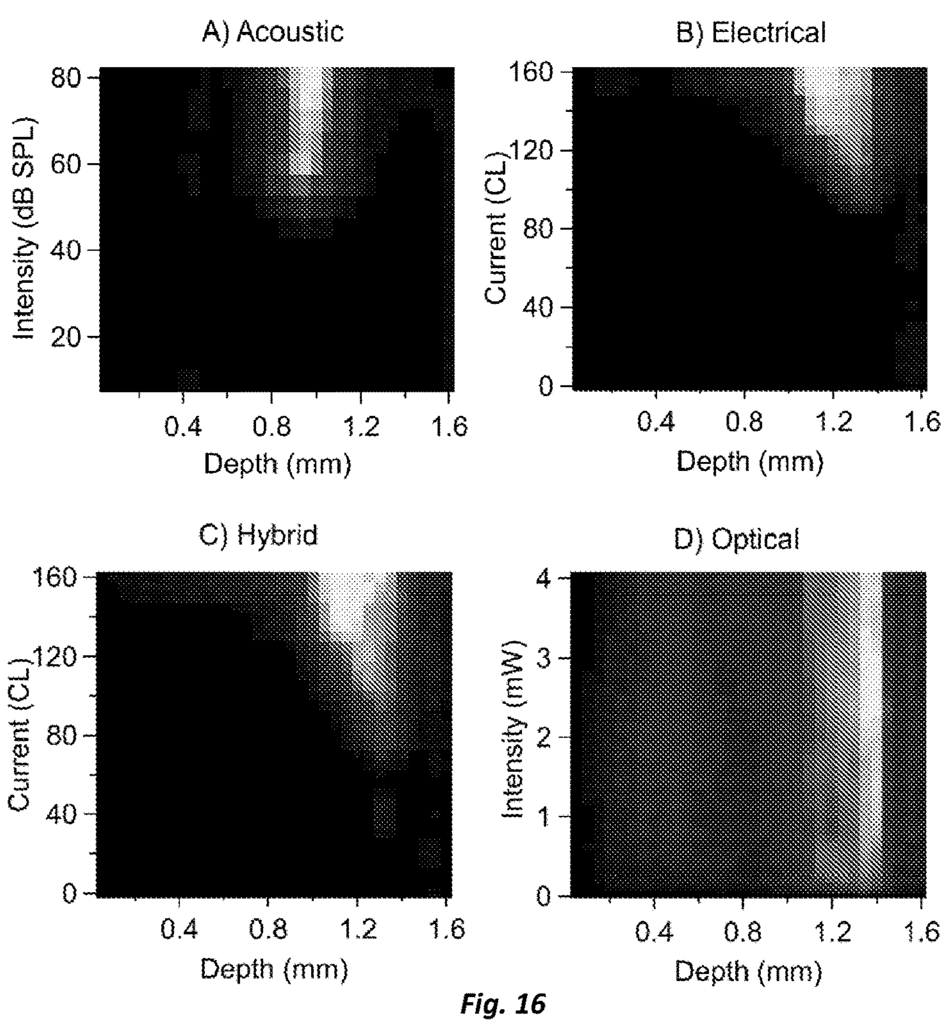
FIG. 16 shows images of the response of the inferior colliculus (IC) of a normal hearing ChR2-H134 mouse generated in response to acoustic stimuli (panel A) and of the inferior colliculus response in acutely deafened ChR2-H134R transgenic mice to electrical, hybrid stimuli and optical stimuli (panels B, C, D)

Referring to FIG. 16, images of the response of the inferior colliculus (IC) of a normal hearing ChR2-H134 mouse were generated in response to acoustic stimuli. Similar images were generated of the inferior colliculus response in acutely deafened ChR2-H134R transgenic mice to electrical, optical stimuli and hybrid stimuli. Optical stimulation pulses were 1 ms, electrical pulses were 250 μs, hybrid stimulation used $t_d$=750 μs so the optical and electrical pulses ended together. For the hybrid stimulation, the optical stimuli were subthreshold while the electrical stimuli ranged from sub- to suprathreshold.

FIG. 16A shows an IC response image and spatial tuning curve (STC) to a 12 kHz pure tone acoustic stimulus in a normal hearing ChR2-H134R transgenic mouse. FIGS. 16B-D show IC response images and STCs for basal turn electrical, hybrid or optical stimulation in an acutely deafened mouse, where the optical fibre and platinum wire were inserted 2 mm through the round window membrane. In each image the firing rate is indicated by tone, where black indicates a spontaneous neural firing rate and white indicates the maximum neural firing rate. In all cases, the width of the STC increased with increasing stimulus intensity above threshold. Optical responses were not detected in mice that did not express ChR2-H134R.

The spread of activation was compared for acoustic, optical, electrical and hybrid stimulation at the base of the cochlea. All modalities resulted in lowest stimulation thresholds in the more ventral recording electrodes, indicative of activation of the base of the cochlea. Electrical and optical responses were spatially broader than acoustic.

Figure 17:
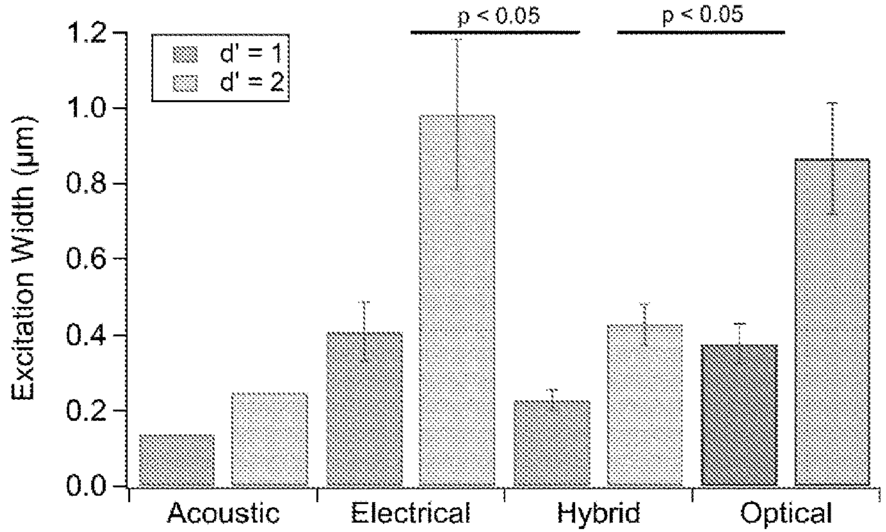
FIG. 17 shows the width of excitation assessed at intensities of different discrimination index levels (d') above threshold.

The width of excitation was assessed at intensities of different discrimination index levels (d': a measure of sensitivity or discriminability derived from signal detection theory) above threshold to control for differences in linearity of stimuli. The width of the STC was taken at levels of d'=1 and d'=2 above threshold. FIG. 17 shows the STC width was significantly wider for optical and electrical stimulation compared to hybrid stimulation. There was no significant difference between optical only and electrical only stimulation.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for stimulating neural tissue, the tissue including one or more neurons genetically modified to express a light-sensitive protein, the method comprising:

applying a light stimulus to the neural tissue, wherein the light stimulus comprises light in the visible spectrum and is configured to activate the light-sensitive protein, wherein the light stimulus is applied as a series of pulses; and applying a respective electrical stimulus to the neural tissue at the same time as, or at a predetermined delay time after, the start of the applying of each pulse of the light stimulus, wherein each electrical stimulus comprises a pulse train;

wherein the combination of the applying of the light stimulus and the applying of the electrical stimulus triggers membrane depolarisation in at least one of the neurons.

2. The method of claim 1, wherein the membrane depolarisation comprises an action potential.

3. The method of claim 1, wherein a light power level of the light stimulus is below a threshold light power level to trigger an action potential in the at least one neuron in the absence of the electrical stimulus.

4. The method claim 1, wherein an electrical power level of the electrical stimulus is below a threshold electrical power level to trigger an action potential in the at least one neuron in the absence of the light stimulus.

5. The method of claim 1, wherein the applying of the electrical stimulus starts at a predetermined delay time after the start of the applying of the light stimulus.

6. The method of claim 5, wherein the predetermined delay time is greater than a duration of the light stimulus, such that the applying of the electrical stimulus starts after cessation of the applying of the light stimulus.

7. The method of claim 6 wherein the predetermined delay time is between 0.1 ms and 30 ms.

8. The method of claim 6, wherein the applying of the electrical stimulus starts between 0.1 ms and 60 ms, after cessation of the applying of the light stimulus, or wherein the applying of the electrical stimulus starts 0.1 ms, 0.2 ms, 0.5 ms, 1 ms, 5 ms, 10 ms, 15 ms, 20 ms, 25 ms, 30 ms, 40 ms, 50 ms, 60 ms, 0.1 s, 0.2 s, 0.3 s, 0.4 s, 0.5 s, 0.6 s, 0.8 s, 1 s, 2 s, 3 s, 4 s, 5 s, 10 s, 15 s, 20 s, 30 s, 45 s, 1 minute, 2 minutes, 5 minutes, 10 minutes, 15 minutes, 20 minutes, 25 minutes, or 30 minutes, after the cessation of the applying of the light stimulus.

9. The method of claim 5, wherein the predetermined delay time is less than a duration of the light stimulus, such that the applying of the electrical stimulus starts before cessation of the applying of the light stimulus.

10. The method of claim 1, wherein a duration of the light stimulus is between 0.1 ms and 20 ms.

11. The method of claim 1, wherein the light stimulus comprises light having a wavelength of between 380 nm and 740 nm.

12. The method of claim 1, wherein the light stimulus comprises light having a wavelength of between 450 nm and 600 nm, or wherein the light stimulus comprises light having a wavelength of less than 700 nm.

13. The method of claim 1, wherein the pulse train has a pulse frequency of between:

5 Hz to 5 kHz; or

500 Hz to 2 kHz; or

5 Hz to 100 Hz.

14. An apparatus configured to stimulate neural tissue, the tissue including one or more neurons genetically modified to express a light-sensitive protein, the apparatus comprising:

a light stimulation device configured to selectively apply, as a series of pulses, a light stimulus to the neural tissue, the light stimulus comprising light in the visible spectrum selected to activate the light-sensitive protein; and an electrical stimulation device configured to selectively apply, as a pulse train, an electrical stimulus to the neural tissue, the electrical stimulus applied to the neural tissue at the same time as, or at a predetermined delay time after, the start of applying of each pulse of light stimulus;

thereby triggering membrane depolarisation in at least one of the neurons.

15. The apparatus of claim 14, comprising a system controller for controlling the applying of the light stimulus and the electrical stimulus, wherein the system controller is configured to trigger application of the electrical stimulus the predetermined delay time after triggering application of the light stimulus.

16. The apparatus of claim 14, further comprising a system controller for controlling the applying of the light stimulus and the electrical stimulus, wherein the system controller is configured to control a duration and/or a power level of the electrical and light stimuli.

17. The apparatus of claim 14, further comprising a recording device for detecting a response of the neural tissue to the light and/or electrical stimuli.

18. The apparatus of claim 17 wherein the system controller is configured to adjust one or more parameters of the electrical and/or light stimuli based on the detected response of the neural tissue to the light and/or electrical stimuli.

* * * * *